(12) United States Patent
Deggerdal et al.

(10) Patent No.: US 8,691,969 B2
(45) Date of Patent: *Apr. 8, 2014

(54) ISOLATION OF NUCLEIC ACID

(75) Inventors: Arne Helge Deggerdal, Fjerdingby (NO); Frank Larsen, Oslo (NO)

(73) Assignee: Life Technologies AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 13/160,428

(22) Filed: Jun. 14, 2011

(65) Prior Publication Data

US 2011/0251382 A1 Oct. 13, 2011

Related U.S. Application Data

(63) Continuation of application No. 12/054,332, filed on Mar. 24, 2008, now Pat. No. 7,989,614, which is a continuation of application No. 11/671,426, filed on Feb. 5, 2007, now abandoned, which is a continuation of application No. 11/234,001, filed on Sep. 23, 2005, now Pat. No. 7,173,124, which is a continuation of application No. 08/849,686, filed as application No. PCT/GB95/02893 on Dec. 12, 1995, now abandoned.

(30) Foreign Application Priority Data

Dec. 12, 1994 (GB) .................................. 9425138.6

(51) Int. Cl.
 *C07H 21/00* (2006.01)
(52) U.S. Cl.
 USPC .................. 536/25.4; 536/25.41; 536/25.42
(58) Field of Classification Search
 None
 See application file for complete search history.

(56) References Cited

U.S. PATENT DOCUMENTS

| | | | |
|---|---|---|---|
| 3,509,024 A | 4/1970 | Jurgens et al. | |
| 4,055,469 A | 10/1977 | Snoke et al. | |
| 4,336,173 A | 6/1982 | Ugelstad | |
| 4,379,843 A | 4/1983 | Cashion | |
| 4,384,933 A | 5/1983 | Takasaki et al. | |
| 4,435,509 A | 3/1984 | Berthold et al. | |
| 4,459,378 A | 7/1984 | Ugelstad | |
| 4,648,975 A | 3/1987 | Barkatt et al. | |
| 4,654,267 A | 3/1987 | Ugelstad et al. | |
| 4,672,040 A | 6/1987 | Josephson | |
| 4,695,537 A * | 9/1987 | Dorsett .............................. 435/5 |
| 4,710,472 A | 12/1987 | Saur et al. | |
| 4,732,811 A | 3/1988 | Margel | |
| 4,772,550 A | 9/1988 | Greenquist et al. | |
| 4,808,521 A | 2/1989 | Allen | |
| 4,843,012 A | 6/1989 | DeBonville | |
| 4,861,705 A | 8/1989 | Margel et al. | |
| 4,871,433 A | 10/1989 | Wagner et al. | |
| 4,874,813 A | 10/1989 | O'Shannessy | |
| 4,889,916 A | 12/1989 | Packard et al. | |
| 4,897,444 A | 1/1990 | Brynes et al. | |
| 4,908,318 A | 3/1990 | Lerner | |
| 4,910,148 A | 3/1990 | Sorensen et al. | |
| 4,920,061 A | 4/1990 | Poynton et al. | |
| 4,921,805 A | 5/1990 | Gebeyehu et al. | |
| 4,923,978 A | 5/1990 | McCormick | |
| 4,935,342 A | 6/1990 | Seligson et al. | |
| 4,950,712 A | 8/1990 | Letourneur et al. | |
| 4,952,519 A | 8/1990 | Lau | |
| 4,957,605 A | 9/1990 | Hurwitt et al. | |
| 4,997,932 A | 3/1991 | Reardon et al. | |
| 5,000,635 A | 3/1991 | Jensen et al. | |
| 5,019,416 A | 5/1991 | Honzawa | |
| 5,030,697 A | 7/1991 | Hugl et al. | |
| 5,032,281 A | 7/1991 | Nagamatsu et al. | |
| 5,053,326 A | 10/1991 | Renz | |
| 5,055,556 A | 10/1991 | Stryer et al. | |
| 5,057,426 A | 10/1991 | Henco et al. | |
| 5,076,950 A | 12/1991 | Ullman et al. | |
| 5,079,155 A | 1/1992 | Cox et al. | |
| 5,084,169 A | 1/1992 | Noble et al. | |
| 5,124,444 A | 6/1992 | Van Ness et al. | |
| 5,126,028 A | 6/1992 | Hurwitt et al. | |
| 5,128,247 A | 7/1992 | Koller | |
| 5,155,018 A | 10/1992 | Gillespie et al. | |
| 5,183,809 A | 2/1993 | Weisz et al. | |
| 5,204,246 A | 4/1993 | Jhingan | |
| 5,234,809 A | 8/1993 | Boom et al. | |
| 5,234,824 A | 8/1993 | Mullis | |
| 5,234,924 A | 8/1993 | Taverne et al. | |
| 5,296,347 A | 3/1994 | LaMotte, III | |

(Continued)

FOREIGN PATENT DOCUMENTS

| AU | 27636/88 | 9/1989 |
|---|---|---|
| CA | 2157968 | 11/2009 |

(Continued)

OTHER PUBLICATIONS

Lund et al. Nucleic Acid Research (1988), vol. 16, pp. 10861-10880.*
6,914,137, "Isolation of Nucleic Acids", www.freepatentsonline.com/6914137.html, Nov. 2007, 35 pgs.
Abramson, "Nucleic acid amplification technologies", *Current Opinion in Biotechnologies* vol. 4, No. 1, 1993, 41-47.
Barclay, "The Leucocyte Antigen Factsbook", *Academic Press*, Second Edition, Elsevier 1997, 613 pgs.
Bianchi, "Isolation of Fetal DNA From Nucleated Erythrocytes in Maternal Blood", The *Proceedings of the National Academy of Sciences*, vol. 87, No. 2 May 1990, 3279-3283.
Biswas et al., "Detection of *Ehrlichia risticii* Feces of Infected Horses by Immunomagnetic Separation and PCT, Journal of Clinical Microbiology", vol. 32, No. 9, Sep. 1994, 2147-2151.

(Continued)

Primary Examiner — Patrick Lewis

(57) ABSTRACT

The present invention provides a method of isolating nucleic acid from a sample, said method comprising contacting said sample with a detergent and a solid support, whereby soluble nucleic acid in said sample is bound to the support, and separating said support with bound nucleic acid from the sample. Where the method of the invention is used to isolate DNA, it may conveniently be couple with a further step to isolate RNA from the same sample.

17 Claims, 7 Drawing Sheets

(56) References Cited

U.S. PATENT DOCUMENTS

| | | |
|---|---|---|
| 5,329,000 A | 7/1994 | Woodard et al. |
| 5,334,499 A | 8/1994 | Burdick et al. |
| 5,342,931 A | 8/1994 | Woodward et al. |
| 5,433,847 A | 7/1995 | Rice |
| 5,455,157 A | 10/1995 | Hinzpeter et al. |
| 5,491,223 A | 2/1996 | Okamoto |
| 5,503,816 A | 4/1996 | Woodard et al. |
| 5,508,164 A | 4/1996 | Kausch et al. |
| 5,510,084 A | 4/1996 | Cros et al. |
| 5,512,439 A | 4/1996 | Hornes et al. |
| 5,523,231 A | 6/1996 | Reeve |
| 5,538,872 A | 7/1996 | Bahl et al. |
| 5,582,988 A | 12/1996 | Backus et al. |
| 5,596,092 A | 1/1997 | Schneider |
| 5,599,667 A | 2/1997 | Arnold, Jr. et al. |
| 5,612,473 A | 3/1997 | Wu et al. |
| 5,616,467 A | 4/1997 | Olsen et al. |
| 5,622,822 A | 4/1997 | Ekeze et al. |
| 5,625,054 A | 4/1997 | Woodard et al. |
| 5,631,146 A | 5/1997 | Szostak |
| 5,641,628 A | 6/1997 | Bianchi |
| 5,652,348 A | 7/1997 | Burton et al. |
| 5,654,179 A | 8/1997 | Lin |
| 5,660,984 A | 8/1997 | Davis et al. |
| 5,672,659 A | 9/1997 | Shalaby et al. |
| 5,677,199 A | 10/1997 | Arrhenuis |
| 5,696,251 A | 12/1997 | Arnold, Jr. et al. |
| 5,705,628 A | 1/1998 | Hawkins |
| 5,710,028 A | 1/1998 | Eyal et al. |
| 5,711,915 A | 1/1998 | Siegmund et al. |
| 5,762,903 A | 6/1998 | Park et al. |
| 5,770,712 A | 6/1998 | Roy et al. |
| 5,780,319 A | 7/1998 | Maxfield Wilson et al. |
| 5,797,202 A | 8/1998 | Akesaka |
| 5,807,527 A | 9/1998 | Burgoyne |
| 5,898,071 A | 4/1999 | Hawkins |
| 5,907,016 A | 5/1999 | Velander et al. |
| 5,914,367 A | 6/1999 | Dordick et al. |
| 5,916,746 A | 6/1999 | Cobbs et al. |
| 5,945,525 A | 8/1999 | Uematsu et al. |
| 5,958,788 A | 9/1999 | Johnson et al. |
| 5,962,412 A | 10/1999 | Hogan, Jr. |
| 5,981,235 A | 11/1999 | Shultz et al. |
| 5,981,735 A | 11/1999 | Thatcher et al. |
| 6,010,867 A | 1/2000 | Kobayashi et al. |
| 6,027,945 A | 2/2000 | Smith et al. |
| 6,051,380 A | 4/2000 | Sosnowski et al. |
| 6,060,246 A | 5/2000 | Summerton et al. |
| 6,090,288 A | 7/2000 | Berglund et al. |
| 6,113,906 A | 9/2000 | Greenwald et al. |
| 6,120,985 A | 9/2000 | Laugharn, Jr. et al. |
| 6,194,562 B1 | 2/2001 | Smith et al. |
| 6,203,768 B1 | 3/2001 | McCormick et al. |
| 6,207,381 B1 | 3/2001 | Larsson et al. |
| 6,218,531 B1 | 4/2001 | Ekenberg |
| 6,255,477 B1 | 7/2001 | Kleiber et al. |
| 6,270,970 B1 | 8/2001 | Smith et al. |
| 6,284,470 B1 | 9/2001 | Bitner et al. |
| 6,287,765 B1 | 9/2001 | Cubicciotti |
| 6,310,199 B1 | 10/2001 | Smith et al. |
| 6,342,387 B1 | 1/2002 | Hayashizaki et al. |
| 6,365,362 B1 | 4/2002 | Terstappen et al. |
| 6,368,800 B1 | 4/2002 | Smith et al. |
| 6,406,913 B1 | 6/2002 | Ullman et al. |
| 6,440,748 B1 | 8/2002 | Katerkamp et al. |
| 6,448,091 B1 | 9/2002 | Massey et al. |
| 6,473,586 B2 | 10/2002 | Noda et al. |
| 6,489,160 B2 | 12/2002 | Hashimoto |
| 6,534,262 B1 | 3/2003 | McKernan et al. |
| 6,545,151 B2 | 4/2003 | Terasawa et al. |
| 6,562,573 B2 | 5/2003 | Halaka |
| 6,582,907 B1 | 6/2003 | Epps et al. |
| 6,627,748 B1 | 9/2003 | Ju et al. |
| 6,635,420 B1 | 10/2003 | Hosel et al. |
| 6,645,733 B1 | 11/2003 | Daksis et al. |
| 6,660,533 B2 | 12/2003 | Mallet et al. |
| 6,677,164 B1 | 1/2004 | Thoma et al. |
| 6,723,510 B2 | 4/2004 | Lubenow et al. |
| 6,743,586 B2 | 6/2004 | Marino et al. |
| 6,811,973 B1 | 11/2004 | Reich |
| 6,811,980 B2 | 11/2004 | Ford et al. |
| 6,818,394 B1 | 11/2004 | O'Donnell-Maloney et al. |
| 6,833,257 B2 | 12/2004 | Lee et al. |
| 6,881,536 B1 | 4/2005 | Shah et al. |
| 6,914,137 B2 | 7/2005 | Baker |
| 6,919,200 B2 | 7/2005 | Ibrahim |
| 6,956,077 B1 | 10/2005 | Akiyama et al. |
| 6,969,603 B2 | 11/2005 | Hayashizaki et al. |
| 7,018,610 B2 | 3/2006 | Hunter et al. |
| 7,056,682 B2 | 6/2006 | Kamei et al. |
| 7,078,536 B2 | 7/2006 | Ge et al. |
| 7,122,659 B2 | 10/2006 | Nikiforov |
| 7,173,124 B2 | 2/2007 | Deggerdal et al. |
| 7,183,116 B2 | 2/2007 | Aebersold et al. |
| 7,262,006 B1 | 8/2007 | Belly et al. |
| 7,338,805 B2 | 3/2008 | Bourget et al. |
| 2001/0018513 A1 | 8/2001 | Baker |
| 2001/0041795 A1 | 11/2001 | Halaka |
| 2002/0009744 A1 | 1/2002 | Bogdanov |
| 2002/0058278 A1 | 5/2002 | Stefano et al. |
| 2002/0164674 A1 | 11/2002 | Tsien et al. |
| 2002/0182169 A1 | 12/2002 | Hunter et al. |
| 2003/0044777 A1 | 3/2003 | Beattie |
| 2003/0099954 A1 | 5/2003 | Miltenyi et al. |
| 2003/0124742 A1 | 7/2003 | Prakash |
| 2003/0130499 A1 | 7/2003 | Baker |
| 2003/0147958 A1 | 8/2003 | Ahn et al. |
| 2003/0211508 A1 | 11/2003 | Ge et al. |
| 2003/0229013 A1 | 12/2003 | Wu et al. |
| 2004/0009506 A1 | 1/2004 | Stephan et al. |
| 2004/0077019 A1 | 4/2004 | Gstach |
| 2004/0092449 A1 | 5/2004 | Ekwuribe |
| 2004/0152084 A1 | 8/2004 | Slattum et al. |
| 2004/0219556 A1 | 11/2004 | Bazan et al. |
| 2004/0259082 A1 | 12/2004 | Williams |
| 2005/0123932 A1 | 6/2005 | Astatke |
| 2006/0035208 A1 | 2/2006 | Roget et al. |
| 2006/0036028 A1 | 2/2006 | Moody et al. |
| 2006/0194202 A1 | 8/2006 | Schatz et al. |
| 2006/0204584 A1 | 9/2006 | Harper et al. |
| 2006/0263780 A1 | 11/2006 | Baker et al. |
| 2007/0117972 A1 | 5/2007 | Halaka |
| 2007/0190559 A1 | 8/2007 | Deggerdal et al. |
| 2007/0231892 A1 | 10/2007 | Baker |
| 2008/0261202 A1 | 10/2008 | Baker et al. |
| 2008/0293035 A1 | 11/2008 | Bergholtz et al. |
| 2008/0300396 A1 | 12/2008 | Deggerdal et al. |
| 2009/0068724 A1 | 3/2009 | Deggerdal et al. |
| 2009/0149646 A1 | 6/2009 | Deggerdal et al. |

FOREIGN PATENT DOCUMENTS

| | | |
|---|---|---|
| DE | 4038293 | 6/1992 |
| DE | 4237381 | 4/1994 |
| DK | 3639949 | 1/1999 |
| EP | 3509024 | 4/1970 |
| EP | 106873 | 2/1984 |
| EP | 0254616 | 1/1988 |
| EP | 0270017 | 6/1988 |
| EP | 0276138 | 7/1988 |
| EP | 0281390 | 7/1988 |
| EP | 0301899 | 2/1989 |
| EP | 0338591 | 10/1989 |
| EP | 0268946 | 3/1990 |
| EP | 0366438 | 5/1990 |
| EP | 0368092 | 5/1990 |
| EP | 0167488 | 7/1990 |
| EP | 0389063 | 9/1990 |
| EP | 0512767 | 11/1992 |
| EP | 5183809 | 2/1993 |
| EP | 0268946 | 9/1993 |
| EP | 0416748 | 3/1994 |
| EP | 0515484 | 4/1996 |
| EP | 0707077 | 4/1996 |

(56) References Cited

FOREIGN PATENT DOCUMENTS

| EP | 0832897 | 4/1998 |
|---|---|---|
| EP | 0834729 | 4/1998 |
| EP | 0853123 | 7/1998 |
| EP | 0885958 | 12/1998 |
| EP | 0897978 | 2/1999 |
| EP | 0502589 | 9/2001 |
| EP | 114506 | 8/2004 |
| GB | 2009272 | 6/1979 |
| GB | 2272391 | 5/1994 |
| GB | 9425138 | 2/1995 |
| GB | 2282138 | 3/1995 |
| JP | 10057056 | 3/1998 |
| WO | WO-86/00139 | 1/1986 |
| WO | WO-86/05815 | 10/1986 |
| WO | WO-88/09201 | 12/1988 |
| WO | WO-90/04019 | 4/1990 |
| WO | WO-90/06042 | 6/1990 |
| WO | WO-90/08159 | 7/1990 |
| WO | WO-90/14891 | 12/1990 |
| WO | WO-91/07660 | 5/1991 |
| WO | WO-91/08308 | 6/1991 |
| WO | WO-91/12079 | 8/1991 |
| WO | WO-92/07863 | 5/1992 |
| WO | WO-92/17609 | 10/1992 |
| WO | WO-93/03167 | 2/1993 |
| WO | WO-93/25709 | 12/1993 |
| WO | WO-93/25912 | 12/1993 |
| WO | WO-94/08239 | 4/1994 |
| WO | WO-94/11103 | 5/1994 |
| WO | WO-95/13368 | 5/1995 |
| WO | WO-95/27718 | 10/1995 |
| WO | WO-96/00228 | 1/1996 |
| WO | WO-96/08500 | 3/1996 |
| WO | WO-96/09116 | 3/1996 |
| WO | WO-96/18731 | 6/1996 |
| WO | WO-96/36706 | 11/1996 |
| WO | WO-96/41810 | 12/1996 |
| WO | WO-96/41811 | 12/1996 |
| WO | WO-97/10331 | 3/1997 |
| WO | WO-97/29825 | 8/1997 |
| WO | WO-97/31105 | 8/1997 |
| WO | WO-97/36004 | 10/1997 |
| WO | WO-98/51693 | 11/1998 |
| WO | WO-99/22020 | 5/1999 |
| WO | WO-99/22021 | 5/1999 |
| WO | WO-99/29703 | 6/1999 |
| WO | WO-00/29848 | 5/2000 |
| WO | WO-00/42432 | 7/2000 |
| WO | WO-00/44928 | 8/2000 |
| WO | WO-00/49031 | 8/2000 |
| WO | WO-00/58329 | 10/2000 |
| WO | WO-00/61806 | 10/2000 |
| WO | WO-00/65041 | 11/2000 |
| WO | WO-00/69872 | 11/2000 |
| WO | WO-00/70040 | 11/2000 |
| WO | WO-00/70041 | 11/2000 |
| WO | WO-01/94572 | 12/2001 |
| WO | WO-02/10373 | 2/2002 |
| WO | WO-02/16580 | 2/2002 |
| WO | WO-02/48164 | 6/2002 |
| WO | WO-2004/055213 | 7/2004 |
| WO | WO-2006/018731 | 2/2006 |

OTHER PUBLICATIONS

Bitner, "Use of MagneSil Paramagnetic Particles for Plasmid Purification, PRC Cleanup, and Purification of Dideoxy and Big Dye DNA Sequencing Reactions", *Proceedings of SPIE*, vol. 3926, Jan. 2000, 126-133.

Brinchmann, "Direct Immunomagnetic Quantification of Lymphocyte Subsets in Blood", *Clinical & Experimental Immunology*, vol. 71, No. 1, Jan. 1988, 182-186.

Bussow, "A Method for Global Protein Expression and Antibody Screening on High-Density Filters of an Arrayed cDNA Library", *Nucleic Acids Research*, vol. 26, No. 21, 1998, 5007-5008.

Chen, "Rolling and Transient Tethering of Leukocytes on Antibodies Reveal Specializations of Selections", *Proceedings of the National Academy of Sciences*, vol. 94, Apr. 1997, 3172-3177.

Cook, "A General Method for Preparing Intact Nuclear DNA", *The EMBO Journal*, vol. 3, No. 8, 1984, 1837-1842.

Database WPI, "Abstract", *Derwent Publications Ltd.* London, GB; AN 1992-077588, XP002295078 & SU 1 638 162 A (As SIBE Cytology) Mar. 30, 1991.

De Latour, "Magnetic Separation in Water Pollution Control—11", *IEEE Transactions on Magnetics*, vol. Mag-11, No. 5, Sep. 1975, 1570-1572.

Eberwine, "Amplification of mRNA Populations Using a RNA Generated from Immobilized Oligo(dT)-T7 Orimed cDNA", *Biotechniques*, vol. 20, No. 4, Apr. 1996, 584-591.

Enk et al., "Extraction and Quantitation of Cytokine mRNA from Human Epidermal Blister Roofs," *Archives of Dermatological Research*, vol. 287, vol. 1, 1994, 72-77.

Fellmann, "Simplified Protocol of Solid-Phase cDNA Libraries for Multiple PCR Amplification", *Biotechniques* vol. 21, No. 5, 1996, 766,768 and 770.

Author Unknown, *Fluka Catalog*, 1995/1996, 1394.

Freifelder, "Chromatography", *Physical Biochemistry* Applications to Biochemistry and Molecular Biology, Second Edition, Chapter 8 1982, 216-275.

George, "Rapid Isolation of Human Endothelial Cells from Whole Blood Using S-Endo1 Monoclonal Antibody Coupled to Immuno-Magnetic Beads: Demonstration of Endothelial Injury after Angioplasty", *Thrombosis and Haemostasis*, vol. 67, No. 1, 1992, 147-153.

Glee, "Methods for DNA Extraction from *Candida albicans* ", *Analytical Biochemistry*, vol. 164, 1987, 207-213.

Invitrogen, "Dynabeads Epithelial Enrich", http://tools.invitrogen.com/content/sfs/manuals/16102-Dynabeads-Epithelial-Enrich-(rev004).pdf Version 4, 2006, 1-2.

Invitrogen, "Dynal Magnetic Beads aka Dynabeads, The Attraction is Simply Magnetisk", http://www.invitrogen.com/site/us/en/home/brands/Dynal.html 2008, 1-4.

Invitrogen, "MSDS Dynabeads M-270 Streptavidin", https://tools.invitrogen.com/content/sfs/msds/DYNABEADS%20M270%20STREPTAVIDIN_MTR-NAIV_EN.pdf, Jan. 17, 2008, 1-5.

Invitrogen, "User Manual for Bead Retrieve", *Dynal Biotech* Version 3, 2005, 1-60.

Jackson, "A General Method for Preparing Chromatin Containing Intact DNA", *The EMBO Journal*, vol. 4, No. 4, 1985, 913-918.

Jakobsen et al. Nucleic Acids Research, 1990, vol. 18, Issue 12, 3669.

Konat, "Rapid Isolation of Genomic DNA from Animal Tissue", *Experimental Cell Research*, vol. 190, 1990, 294-296.

Leadon, "A Rapid and Mild Procedure for the Isolation of DNA from Mammalian Cells", *Analytical Biochemistry*, vol. 120, 1982, 282-288.

Li, "Construction and Application of Prokaryotic Vector which Expresses the Protein that Can be Quickly Purified by IMAC", *Chinese Journal of Biotechnology* vol. 13, No. 1, 1997, 37-42.

Lu, "Combined pH Gradient and Anion-Exchange High-Performance Liquid Chromatographic Separation of Oligodeoxyribonucleotides", *Journal of Chromatography A* vol. 686, 1994, 339-343.

McLauglin, "Mixed-Mode Chromatography of Nucleic Acids", *Chemical Reviews*, vol. 89, No. 2, 1989, 309-319.

Merel, "Completely Automated Extraction of DNA from Whole Blood", *Clinical Chemistry* vol. 42, No. 8 1996, 1285-1286.

Millard, "Fractionation of Mammilian DNA on DEAE-Cellulose", *Journal of Chromatography*, vol. 107, No. 1, Apr. 9, 1975, 125-140.

More, "Quantitative Cell Lysis of Indigenous Microorganisms and Rapid Extraction of Microbial DNA from Sediment", *Applied and Environmental Microbiology*, vol. 60, No. 5, May 1994, 1572-1580.

Natarajan, "Helix-Coil Transitions in DNA Using a pH Variation Methods: Case of a Melting Paradox as a Function of Ionic Strength", *Analytical Biochemistry*, vol. 237, No. 1, May 15, 1996, 152-155.

Olsvik et al., "Magnetic Separation Techniques in Diagnostic Microbiology," *Clinical Microbiology Reviews*, vol. 7, No. 1, Jan. 1994, 43-54.

(56) References Cited

OTHER PUBLICATIONS

Oswald, "Differential biogenesis of photosystem-II in mesophyll and bundle-sheath cells of 'malic' enzyme NADP+-type C4 plants", *European Journal of Biochemistry*, vol. 190, 1990, 185-194.

Pharmacia Biotech Inc., "Affinity Chromography-Coupling Gels Pre-packed Columns and Media: Coupling Gels Selection Guide", *Biotechnology Products Catalog* Now part of GE 1993, 3 pgs.

Pharmacia Biotech Inc., "Introduction (cont.)", *Molecular and Cell Biology Products Catalog* now part of GE 1994, 2 pgs.

Reeck, "Resolution of a Spectrum of Nucleoprotein Species in Sonicated Chromatin", *Proceedings of the National Academy of Sciences*, vol. 69, No. 8, Aug. 15, 1972, 2317-2321.

Riol, "Optimized Lymphocyle Protein Extraction Performed Simultaneously with DNA and RNA Isolation: Application to the Study of Factors Affecting DNA, RNA and Protein Recovery from Lymphocytes of the Oldest Individuals", *Analytical Biochemistry*, vol. 275, 1999, 192-201.

Safarik, "Biologically Active Compounds and Xenobiotics: Magnetic Affinity Separations,", *Institute of Landscape Ecology, Academy of Sciences*, Czech Republic, 2000, 2163-2170.

Sambrook, "Molecular Cloning: A Laboratory Manual, Second Edition", *Cold Spring Harbor Laboratory Press*, Cold Spring Harbor, NY, 1989, 16-66.

Schubler, "Combined isolation of nucleic acids and protein from small amounts of tissue", *TIG* vol. 11, No. 10, Oct. 1995, 378-379.

Slaby, "Rapid Isolation of Homogeneous Cloned T7 Gene 5 Protein and T7 DNA Polymerase by Affinity Chromotography on Immobilized Thioredoxin", *Protein Expression and Purification*, vol. 2, No. 4, Aug. 1991, 270-277.

Smalia, "Rapid DNA Extraction Protocol from Soil for Polymerase Chain Reaction-Mediated Amplification", *Journal of Applied Bacteriology* vol. 74, 1993, 78-85.

Yolken, "Solid phase capture method for the specific amplification of microbial nucleic acids—avoidance of false-positive and false-negative reactions", *Molecular and Cellular Probes* vol. 5, 1991, 151-156.

CA Application No. 2,473,376, Office Action mailed on Aug. 12, 2010.

CN Application No. 03802373.3, Response to Oct. 16, 2009 Office Action filed on Feb. 25, 2010.

CN Application No. 03802373.3, Office Action mailed on Oct. 16, 2009.

EP Application No. 00907058, Supplementary European Search Report, completed on Sep. 7, 2000.

EP Application No. 03768003.0, Office Action mailed on Mar. 30, 2006.

EP Application No. 09594035.1, Office Action mailed on Jan. 23, 2009.

PCT Application No. PCT/GB/03/05496, International Preliminary Report on Patentability mailed on Apr. 26, 2005.

PCT Application No. PCT/GB03/05496, International Search Report mailed on Mar. 18, 2004.

PCT Application No. PCT/GB03/05496, International Written Opinion mailed on Jul. 7, 2004.

PCT Application No. PCT/US2000/002115, International Search Report mailed on Jul. 31, 2000.

PCT Application No. PCT/US2000/002115, International Preliminary Examination Report mailed on Mar. 30, 2001.

JP Application No. 2003-562329, Office Action mailed on Oct. 28, 2009.

JP Application No. 2003-562329, Response to Sep. 1, 2008 Office Action filed on Mar. 2, 2009.

U.S. Appl. No. 08/849,686, Non Final Office Action mailed on Jul. 16, 2003.

U.S. Appl. No. 10/297,301, Non-Final Rejection mailed on Mar. 22, 2006.

U.S. Appl. No. 10/501,162, Office Action mailed on Apr. 27, 2010.

U.S. Appl. No. 10/501,162, Office Action mailed on Oct. 21, 2009.

U.S. Appl. No. 10/501,162, Office Action mailed on Jan. 22, 2009.

U.S. Appl. No. 10/547,644, Office Action mailed on Sep. 27, 2007.

U.S. Appl. No. 11/555,975, Final Office Action mailed on Apr. 6, 2009.

U.S. Appl. No. 11/555,975, Non-Final Office Action mailed on Sep. 19, 2008.

U.S. Appl. No. 11/671,426, Non Final Office Action mailed Sep. 24, 2007.

U.S. Appl. No. 12/052,332, Office Action mailed on Apr. 15, 2010.

U.S. Appl. No. 12/052,332, Office Action mailed on Jun. 17, 2009.

U.S. Appl. No. 12/054,332, Notice of Allowance mailed on Nov. 17, 2010.

U.S. Appl. No. 12/056,858, Office Action mailed on Feb. 20, 2009.

U.S. Appl. No. 12/056,858, Office Action mailed on Oct. 26, 2009.

U.S. Appl. No. 12/130,926, Office Action mailed on Dec. 15, 2009.

U.S. Appl. No. 12/130,959, Office Action mailed on May 28, 2010.

U.S. Appl. No. 12/098,411, Office Action mailed Jul. 14, 2010.

U.S. Appl. No. 12/054,332, Office action mailed on Mar. 21, 2011.

U.S. Appl. No. 12/098,411, Office Action mailed on Oct. 13, 2009.

\* cited by examiner

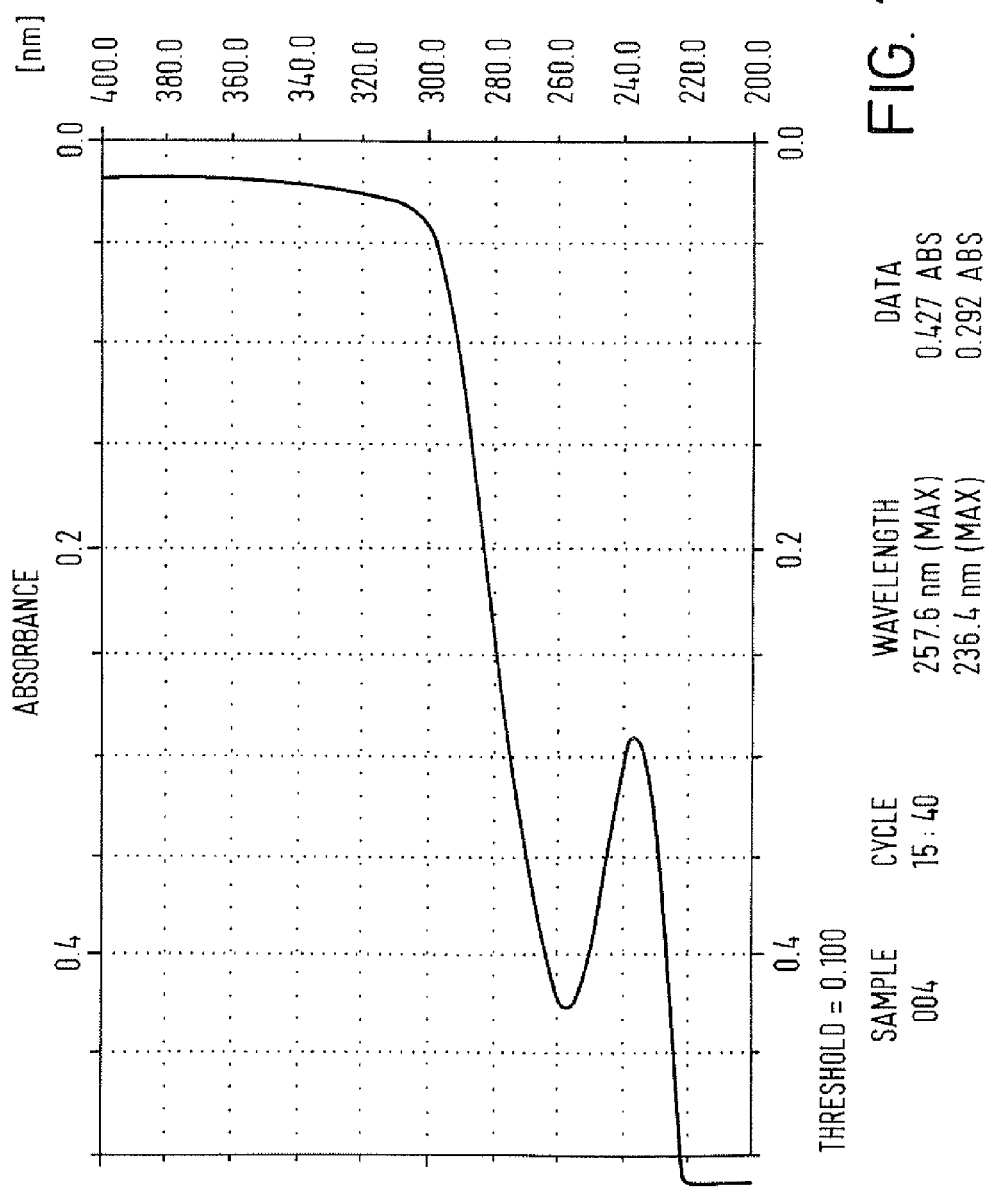

1 2 3

1 2

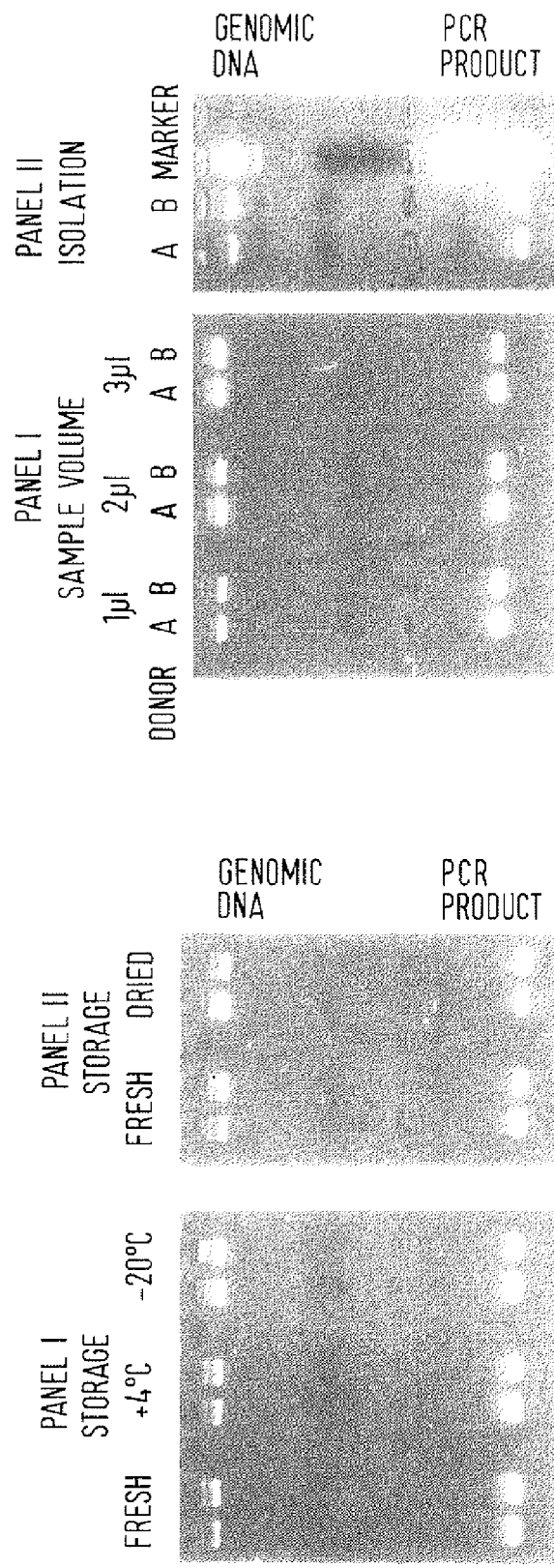

ISOLATION OF NUCLEIC ACID

CROSS-REFERENCE TO RELATED APPLICATIONS

This application is a continuation of, and claims priority under 35 USC §120 to U.S. application Ser. No. 12/054,332, filed Mar. 24, 2008, now allowed, which is a continuation of U.S. application Ser. No. 11/671,426, filed Feb. 5, 2007, which is a continuation of, and claims priority under 35 USC §120 to U.S. application Ser. No. 11/234,001, filed Sep. 23, 2005, now U.S. Pat. No. 7,173,124, which is a continuation of, and claims priority under 35 USC §120 to U.S. application Ser. No. 08/849,686, filed Aug. 21, 1997, now abandoned, which is a 35 USC §371 filing of International Application No. PCT/GB95/02893, filed Dec. 12, 1995, the disclosures of which are incorporated by reference herein in their entireties.

The present invention relates to the isolation of nucleic acid, and especially to the isolation of DNA or RNA from cells.

The isolation of DNA or RNA is an important step in many biochemical and diagnostic procedures. For example, the separation of nucleic acids from the complex mixtures in which they are often found is frequently necessary before other studies and procedures e.g. detection, cloning, sequencing, amplification, hybridisation, cDNA synthesis etc. can be undertaken; the presence of large amounts of cellular or other contaminating material e.g. proteins or carbohydrates, in such complex mixtures often impedes many of the reactions and techniques used in molecular biology. In addition, DNA may contaminate RNA preparations and vice versa. Thus, methods for the isolation of nucleic acids from complex mixtures such as cells, tissues etc. are demanded, not only from the preparative point of view, but also in the many methods in use today which rely on the identification of DNA or RNA e.g. diagnosis of microbial infections, forensic science, tissue and blood typing, detection of genetic variations etc.

In RNA identifications it is important for a conclusive diagnosis to be certain that the detected sequence is derived from an RNA molecule and not from genomic DNA contamination in the sample. For this reason, methods for the separation of RNA from DNA are important. Also, for RNA isolation rapid methods are required since RNA molecules usually are very unstable and rapidly degraded by RNases present in cells and body fluids. The quality of the RNA is probably the most important factor in determining the quality of the final results in protocols utilising mRNA, especially for cDNA synthesis. It is important to avoid DNA contamination of RNA preparations for a number of reasons. Firstly, DNA increases viscosity making sample handling difficult leading to poor RNA yield and also RNA of poor quality with the likelihood of DNA contamination. Also, DNA contamination may trap RNase enzymes and make downstream applications such as RT-PCR worthless.

A range of methods are known for the isolation of nucleic acids, but generally speaking, these rely on a complex series of extraction and washing steps and are time consuming and laborious to perform. Moreover, the use of materials such as alcohols and other organic solvents, chaotropes and proteinases is often involved, which is disadvantageous since such materials tend to interfere with many enzymic reactions and other downstream processing applications.

Thus, classical methods for the isolation of nucleic acids from complex starting materials such as blood or blood products or tissues involves lysis of the biological material by a detergent or chaotrope, possibly in the presence of protein degrading enzymes, followed by several extractions with organic solvents e.g. phenol and/or chloroform, ethanol precipitation, centrifugations and dialysis of the nucleic acids. The purification of RNA from DNA may involve a selective precipitation with LiCl or a selective isolation with acidic guanidinium thiocyanate combined with phenol extractions and ethanol precipitation. Not only are such methods cumbersome and time consuming to perform, but the relatively large number of steps required increases the risk of degradation, sample loss or cross-contamination of samples where several samples are simultaneously processed. In the case of RNA isolation, the risk of DNA contamination is relatively high.

In purification of RNA, it is commonly desired to specifically isolate mRNA. Most mRNA purification strategies involve isolation of total RNA and fractionation of the isolated RNA. Preparation of high-quality mRNA is an important step in the analysis of gene structure and gene regulation.

Most eukaryotic mRNAs have a poly(A)tail, typically about 50 to 300 nucleotides long. Such mRNA is referred to as polyadenylated or poly(A)$^+$ mRNA. In separating this polyadenylated RNA from the non-adenylated RNA which accounts for 95% or more of a cell's total RNA, advantage is taken of this poly(A) tail and some type of affinity separation directed toward the poly(A) tail is performed. The conventional technology has involved purification of total RNA as a first step and selection of poly(A)$^+$ RNA by affinity chromatography using oligo(dT)-cellulose as the second step. This strategy, is rather time-consuming and labour-intensive. An alternative strategy for mRNA purification is to use oligo(dT) linked to solid supports such as microplates, latex, agarose or magnetic beads.

Over the past four years it has become increasingly popular to employ a magnetic bead assisted strategy for poly(A)$^+$ RNA selection since such beads have proven to be favourable in mRNA manipulations. In many approaches, the yield and the quality of the products depends on how rapidly the mRNA can be purified from nucleases and other contaminants. By using the magnetic bead separation technology, pure, intact poly(A)$^+$ RNA can be obtained rapidly either from total RNA preparations or more importantly, directly from crude lysates of solid tissues, cell or body fluids. The entire procedure can be carried out in a microfuge tube without phenol extractions or ethanol precipitations.

One approach common in RNA purification, which may be used in conjunction with the solid phase approach is to carry out the lysis of the biological material and the subsequent hybridisation to oligo dT in LiCl and LiDS/SDS buffers, thereby avoiding extra steps such as phenol extraction or proteinase-K digestion. The whole direct mRNA isolation takes approximately 15 minutes and since the mRNA is stable for more than 30 minutes in the lysis buffer, this ensures the high quality of the mRNA purified. However, a disadvantage of this method is that mRNA per weight unit of tissue is affected by the amount of tissue used and above a critical threshold of lysed cells, the yield of mRNA decreases.

Another common approach for direct mRNA purification is, as mentioned above, to use guanidinium isothiocyanate (GTC) and sarkosyl. A GTC-buffer system is preferred by most researchers due to the ability of this chaotropic salt to inhibit RNases. This may also be used in combination with the magnetic bead approach. However, the viscosity of cell lysates in 4M GTC is high and the beads are not effectively attracted by the magnet, resulting in an increased risk for DNA contamination, both for beads and other solid phases, and lower yields.

More recently, other methods have been proposed which rely upon the use of a solid phase. In U.S. Pat. No. 5,234,809, for example, is described a method where nucleic acids are bound to a solid phase in the form of silica particles, in the presence of a chaotropic agent such as a guanidinium salt, and thereby separated from the remainder of the sample. WO 91/12079 describes a method whereby nucleic acid is trapped on the surface of a solid phase by precipitation. Generally speaking, alcohols and salts are used as precipitants.

Although such methods speed up the nucleic acid separation process, there are disadvantages associated with the use of alcohols, chaotropes, and other similar agents. Chaotropes require to be used at high molarity, resulting in viscous solutions which may be difficult to work with, especially in RNA work. Amplification procedures such as PCR, and other enzyme-based reactions, are very sensitive to the inhibitory or otherwise interfering effects of alcohols and other agents. Moreover, the drying of the nucleic acid pellet which is necessary following alcohol precipitation and the problems with dissolving nucleic acids, are also known to lead to artefacts in enzyme-based procedures such as PCR. Since such procedures are now a mainstay of molecular biology, there is a need for improved methods of nucleic acid isolation, and particularly for methods which are quick and simple to perform and which avoid the use of chaotropic agents or alcohol precipitation. There is also a need for a method which allows for differentiation between RNA and DNA and permits a separate isolation of both types of nucleic acid from the same sample. The present invention seeks to provide such methods.

In particular, it has now been found that nucleic acid may be isolated from a sample in a form suitable for amplification or other downstream processes, by a simple and easy to perform procedure which involves treating the sample with detergent and allowing the nucleic acid to bind to a solid support, whereupon the nucleic acid may be readily separated from the sample, e.g. by removal of the support. The binding of the nucleic acid is independent of its sequence.

In one aspect, the present invention thus provides a method of isolating nucleic acid from a sample, said method comprising contacting said sample with a detergent and a solid support, whereby soluble nucleic acid in said sample is bound to the support, and separating said support with bound nucleic acid from the sample.

The nucleic acid may be DNA, RNA or any naturally occurring or synthetic modification thereof, and combinations thereof. Preferably however the nucleic acid will be DNA, which may be genomic, or, cDNA, and single or double stranded or in any other form.

Where the method of the invention is used to isolate DNA, it may conveniently be coupled with a further step to isolate RNA from the same sample. The use of the method in such two-step RNA separations will be described in more detail below.

The samples may be any material containing nucleic acid, including for example foods and allied products, clinical and environmental samples. However, the sample will generally be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include whole blood and blood-derived products such as plasma, serum and buffy coat, urine, faeces, cerebrospinal fluid or any other body fluids, tissues, cell cultures, cell suspensions etc.

The sample may also include relatively pure starting materials such as a PCR product, or semi-pure preparations obtained by other nucleic acid recovery processes.

The nucleic acid-containing sample may, generally speaking, simply be contacted with the detergent, and a solid phase which may be added to the sample prior to, simultaneously with, or subsequently to the detergent. If necessary, this may be preceded by one or more separate steps to disrupt structural components such as cell walls or to achieve lysis. Procedures for achieving this are well known in the art. Thus, for example, although some cells e.g. blood cells, may be lysed by the detergent alone, other cells, e.g. plant or fungal cells or solid animal tissues may require more vigorous treatment such as, for example, grinding in liquid nitrogen, heating in the presence of detergent, alkaline lysis in the presence of detergent. For samples in the form of paraffin sections and such like, lysis (and melting of the paraffin) may be effected by heating, for example using a microwave oven (Banerjee, S. K. et al., 1995, Biotechniques 18: 769-773). Also, certain more compact tissues may require enzyme treatment, for example using proteinase K to obtain sufficient release of nucleic acid. The various components are mixed and simply allowed to stand for a suitable interval of time to allow the nucleic acid to bind to the support. Conveniently, if other agents such as enzymes e.g. proteinase K are being used, they may be included in with the detergent. The support is then removed from the solution by any convenient means, which will depend of course on the nature of the support, and includes all forms of withdrawing the support away from the sample supernatant, or vice versa, for example centrifugation, decanting, pipetting etc.

The conditions during this process are not critical, and it has been found convenient, for example, simply to mix the sample with the detergent in the presence of a solid phase, and allow it to stand at room temperature, for 5 to 20 minutes, before separating. As mentioned above, the reaction time is not critical and as little as 5 minutes is often enough. However, if convenient, longer periods may be used, e.g. 0.5 to 3 hours, or even overnight. Mixing can be done by any convenient means, including for example simple agitation by stirring or vortexing. Also, if desired, higher or lower temperatures may be used, but are not necessary.

The detergent may be any detergent, and a vast range are known and described in the literature. Thus, the detergent may be ionic, including anionic and cationic, non-ionic or zwitterionic. The term "ionic detergent" as used herein includes any detergent which is partly or wholly in ionic form when dissolved in water. Anionic detergents have been shown to work particularly well and are preferred. Suitable anionic detergents include for example sodium dodecyl sulphate (SDS) or other alkali metal alkylsulphate salts or similar detergents, sarkosyl, or combinations thereof.

Conveniently, the detergent may be used in a concentration of 0.2 to 30% (w/v), e.g. 0.5 to 30%, preferably 0.5 to 15%, more preferably 1 to 10%. For anionic detergents concentrations of 1.0 to 5% e.g. 0.5 to 5% have been shown to work well.

The detergent may be supplied in simple aqueous solution, which may be alkaline or acidic, or more preferably in a buffer. Any suitable buffer may be used, including for example Tris, Bicine, Tricine, and phosphate buffers. Conveniently, a source of monovalent cations, e.g. a salt, may be included to enhance nucleic acid capture, although this is not necessary. Suitable salts include chloride salts, e.g. sodium chloride, lithium chloride etc. at concentrations of 0.1 to 1M, e.g. 250 to 500 mM. As mentioned above, other components such as enzymes, may also be included.

Other optional components in the detergent composition include chelating agents e.g. EDTA, EGTA and other polyamino carboxylic acids conveniently at concentrations of 1 to 50 mM etc., reducing agents such as dithiotreitol (DTT) or β-mercaptoethanol, at concentrations of for example 1 to 10 mM.

Preferred detergent compositions may for example comprise:

100 mM Tris-HCl pH 7.5
10 mM EDTA
2% SDS or:

100 mM TrisCl pH 7.5
10 mM EDTA
5% SDS
10 mM NaCl or:

100 mM TrisCl pH 7.5
500 mM LiCl
10 mM EDTA
1% LiDS

The detergent functions in the method to lyse the nucleic acid containing material, e.g. the cells and nuclei to release the nucleic acid. The detergent is also believed to help to disrupt the binding of proteins, e.g. DNA-binding proteins, to the nucleic acid and to reduce the problem of contaminants in the sample sticking to the solid support.

The solid support may be any of the well known supports or matrices which are currently widely used or proposed for immobilisation, separation etc. These may take the form of particles, sheets, gels, filters, membranes, fibres, capillaries, or microtitre strips, tubes, plates or wells etc.

Conveniently the support may be made of glass, silica, latex or a polymeric material. Preferred are materials presenting a high surface area for binding of the nucleic acid. Although not wishing to be bound by theoretical considerations, it is believed that the nucleic acid binding process may be assisted by the nucleic acid "wrapping around" the support. Such supports will generally have an irregular surface and may be for example be porous or particulate e.g. particles, fibres, webs, sinters or sieves. Particulate materials e.g. beads are generally preferred due to their greater binding capacity, particularly polymeric beads.

Conveniently, a particulate solid support used according to the invention will comprise spherical beads. The size of the beads is not critical, but they may for example be of the order of diameter of at least 1 and preferably at least 2 µm, and have a maximum diameter of preferably not more than 10 and more preferably not more than 6 µm. For example, beads of diameter 2.8 µm and 4.5 µm have been shown to work well.

Monodisperse particles, that is those which are substantially uniform in size (e.g. size having a diameter standard deviation of less than 5%) have the advantage that they provide very uniform reproducibility of reaction. Monodisperse polymer particles produced by the technique described in U.S. Pat. No. 4,336,173 are especially suitable.

Non-magnetic polymer beads suitable for use in the method of the invention are available from Dyno Particles AS (Lillestrøm, Norway) as well as from Qiagen, Pharmacia and Serotec.

However, to aid manipulation and separation, magnetic beads are preferred. The term "magnetic" as used herein means that the support is capable of having a magnetic moment imparted to it when placed in a magnetic field, and thus is displaceable under the action of that field. In other words, a support comprising magnetic particles may readily be removed by magnetic aggregation, which provides a quick, simple and efficient way of separating the particles following the nucleic acid binding step, and is a far less rigorous method than traditional techniques such as centrifugation which generate shear forces which may degrade nucleic acids.

Thus, using the method of the invention, the magnetic particles with nucleic acid attached may be removed onto a suitable surface by application of a magnetic field e.g. using a permanent magnet. It is usually sufficient to apply a magnet to the side of the vessel containing the sample mixture to aggregate the particles to the wall of the vessel and to pour away the remainder of the sample.

Especially preferred are superparamagnetic particles for example those described by Sintef in EP-A-106873, as magnetic aggregation and clumping of the particles during reaction can be avoided, thus ensuring uniform and nucleic acid extraction. The well-known magnetic particles sold by Dynal AS (Oslo, Norway) as DYNABEADS, are particularly suited to use in the present invention.

Functionalised coated particles for use in the present invention may be prepared by modification of the beads according to U.S. Pat. Nos. 4,336,173, 4,459,378 and 4,654,267. Thus, beads, or other supports, may be prepared having different types of functionalised surface, for example positively charged or hydrophobic. Weakly and strongly positively charged surfaces, weakly negatively charged neutral surfaces and hydrophobic surfaces e.g. polyurethane-coated have been shown to work well.

It is also possible to use solid supports which have been modified to permit the selective capture of desired cells, viruses etc. containing the nucleic acid. Thus for example, supports carrying antibodies, or other binding proteins, specific for a desired cell type may be used. This may introduce a degree of selectivity to the isolation of the nucleic acid, since only nucleic acid from a desired target source within a complex mixture may be separated. Thus for example, such a support may be used to separate and remove the desired cell type etc. from the sample, following which, the detergent is added to achieve lysis, release of the nucleic acid, and binding to the support.

The preparation of such selective cell capture matrices is well known in the art and described in the literature.

Likewise, the support may be provided with binding partners to assist in the selective capture of nucleic acids. For example, complementary DNA or RNA sequences, or DNA binding proteins may be used, or viral proteins binding to viral nucleic acid. The attachment of such proteins to the solid support may be achieved using techniques well known in the art.

Although not necessary, it may be convenient to introduce one or more washing steps to the isolation method of the invention, for example following separation of the support from the sample. In the case of magnetic beads, this may conveniently be done before releasing the DNA from the beads. Any conventional washing buffers or other media may be used. Generally speaking, low to moderate ionic strength buffers are preferred e.g. 10 mM Tris-HCl at pH 8.0/10 mM NaCl. Other standard washing media, e.g. containing alcohols, may also be used, if desired.

Following the separation step, and any optional washing steps which may be desired, the support carrying the nucleic acid may be transferred e.g. resuspended or immersed into any suitable medium e.g. water or low ionic strength buffer. Depending on the support and the nature of any subsequent processing desired, it may or may not be desirable to release the nucleic acid from the support.

In the case of a particulate solid support such as magnetic or non-magnetic beads, this may in many cases be used directly, for example in PCR or other amplifications, without eluting the nucleic acid from the support. Also, for many DNA detection or identification methods elution is not necessary since although the DNA may be randomly in contact with the bead surface and bound at a number of points by hydrogen bonding or ionic or other forces, there will generally be sufficient lengths of DNA available for hybridisation to oligonucleotides and for amplification.

However, if desired, elution of the nucleic acid may readily be achieved using known means, for example by heating, e.g. to 65° C. for 5 to 10 minutes, and following which the support may be removed from the medium leaving the nucleic acid in solution. Such heating is automatically obtained in PCR by the DNA denaturation step preceding the cycling program.

If it is desired to remove RNA from DNA, this may be achieved by destroying the RNA before the DNA separation step, for example by addition of an RNAase or an alkali such as NaOH.

Alternatively, as mentioned above, the method of the invention may be used to separate sequentially DNA and RNA from the sample. It may also be used to remove DNA from a sample in an RNA purification procedure.

Conveniently, the sequential separation may take place using two different solid phases, for example solid supports which can differentiate between DNA and RNA. Thus, such a method may comprise carrying out a first step separation to isolate DNA as described above. A further solid support can then be added to the sample to capture the RNA remaining in the sample, either by using a solid support that can bind the RNA or any remaining nucleic acid, or a solid support that can capture specific RNA molecules (e.g. by carrying a complementary nucleic acid probe), or a subset of RNA molecules e.g. polyadenylated RNA. In this way it is possible rapidly to isolate and separate DNA and RNA or subsets of both from the same sample. This may be useful, for example by measuring the isolated DNA to estimate the amount of cells used for RNA extraction, which will give a reference between different samples.

However, the DNA isolation procedure of the invention may also readily be combined, as a preliminary step, with other conventional RNA purification procedures, for example DNA isolation with detergent according to invention may be carried out before a selective RNA precipitation step, for example using LiCl or before RNA separation using GTC and sarkosyl.

In a representative procedure, the sample is lysed in the presence of detergent and the DNA is allowed to bind to a solid support, whereupon the DNA may readily be separated from the sample by removal of the support. If desired, the DNA can rapidly and easily be further handled for amplification or other downstream processes. The RNA may then be isolated. This can be by a solid phase based system as described above, including a repetition of the method of the invention, or by conventional techniques such as extractions, precipitations or affinity chromatography.

A particularly advantageous embodiment of the invention is to use the isolation method of the invention to remove DNA from a sample prior to isolation of RNA, such that the viscosity of the lysed sample is reduced and a specific isolation of RNA molecules is favoured which again reduces or avoids the possibility for DNA contamination of the RNA. Such a method also has the advantage of being quick to perform.

The invention is advantageously amenable to automation, particularly if particles, and especially, magnetic particles are used as the support.

The various reactants and components required to perform the method of the invention may conveniently be supplied in kit form. Such kits represent a further aspect of the invention.

At its simplest, this aspect of the invention provides a kit for isolating nucleic acid from a sample comprising a solid support and one or more detergents.

Optionally included in such a kit may be buffers, salts, lysis agents e.g. proteinases, chelating agents and reducing agents.

For isolation of RNA, the kits may further comprise means for isolating RNA e.g. a second solid support for isolating RNA, for example a support provided with probes for capture of RNA e.g. oligo dT or probes of complementary sequence to the desired target, or a chaotrope or selective precipitating agent.

The invention will now be described in more detail in the following non-limiting Examples with reference to the drawings in which:

FIG. 1 shows as optical density scan of DNA isolated as described in Example 1 (ordinate shows absorbance (OD), abscissa shows wavelength (nM)). Maximum absorbance (0.427) at 257.6 nM; minimum absorbance (0.292) at 236.4 nM; at a threshold of 0.100;

Figure 3:
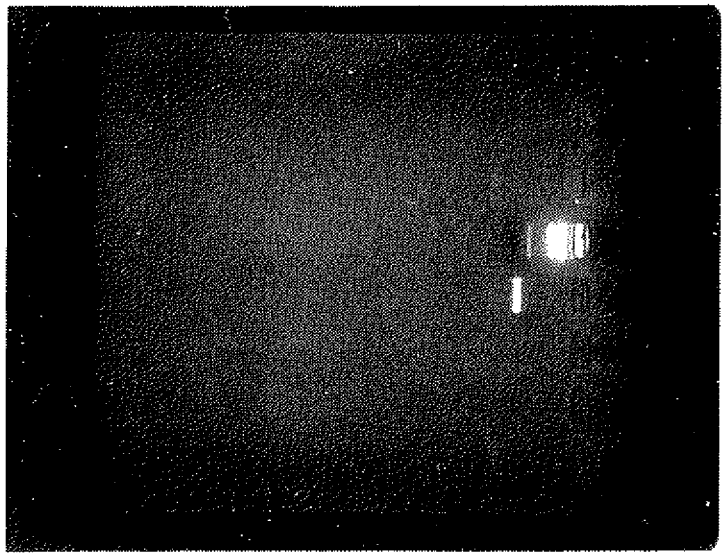
Figure 4:
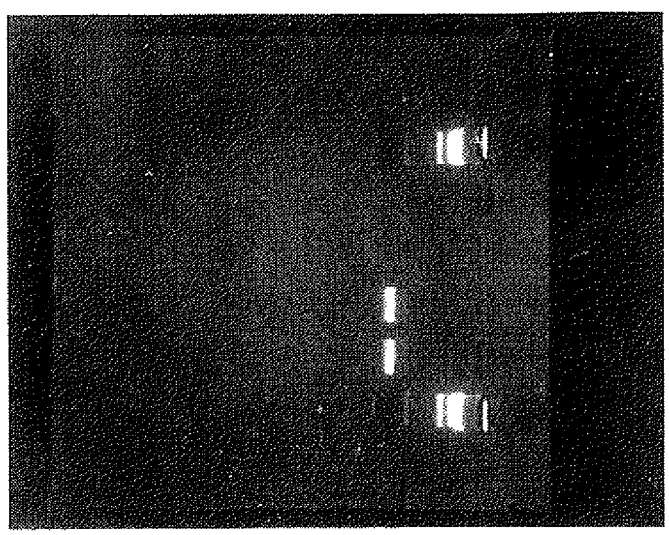

FIG. 3 shows agarose gel electrophoresis of the PCR product of Example 2 (lane 1: PCR product; lane 2: λHind III; lane 3: negative PCR control); and FIG. 4 shows agarose gel electrophoresis of the PCR product of Example 5 (lane 1: λHind III; lanes 2 and 3: isolations A and B respectively; lanes 4 and 5: negative control; lane 6: λHind III).

Figure 5:
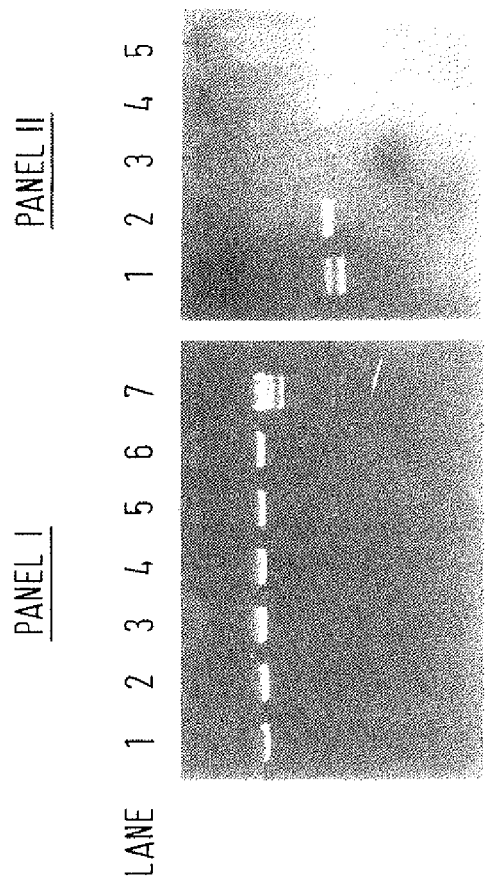

FIG. 5 show the comparison between traditionally isolated DNA and DNA isolated with Dynabeads DNA DIRECT. Panel I shows the amount of genomic DNA isolated from 10 μl of whole blood with Dynabeads DNA DIRECT including the optional elution step (lanes 1 and 2), with Dynabeads DNA DIRECT with the elution step omitted (lanes 3 and 4), and with traditional DNA isolation (lanes 5 and 6). The molecular weight marker in lane 7 is λHindIII. Panel II shows the integrity of DNA isolated by Dynabeads DNA DIRECT. Lanes 1 and 2 show AMXY PCR from 20 ng of DNA isolated with Dynabeads DNA DIRECT from a male and female donor respectively. Lanes 4 and 5 show AMXY PCR from 200 ng DNA isolated by traditional methods from a female and a male donor respectively. Lane 3 is the negative control.

Figure 6:
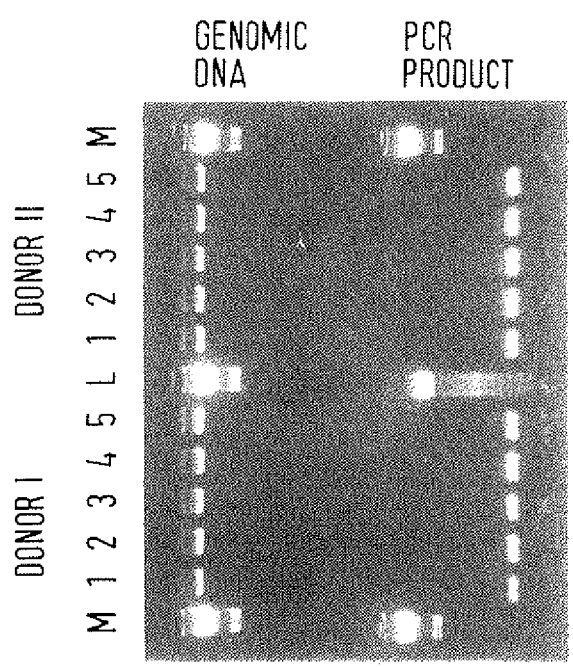

FIG. 6 shows the reproducibility of Dynabeads DNA DIRECT. The figure shows five independent Dynabeads DNA DIRECT isolations from each of two donors. Half of the DNA obtained from 10 μl of blood is shown in the upper part of the figure, 20% of the product from PCR reactions started with 10% of the isolated DNA is shown in the lower part of the figure. Molecular weight markers are λHindIII (lanes marked M) or 100 bp ladder (lane marked L).

Figure 7:
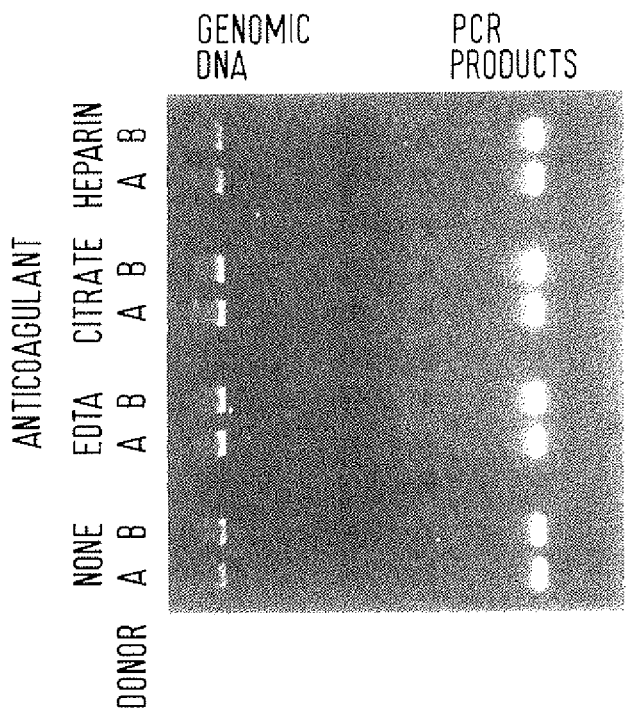

FIG. 7 shows the effect of different anticoagulants. The figure shows Dynabeads DNA DIRECT isolations from whole blood that is not anticoagulated and from blood anticoagulated with EDTA, citrate, or heparin. The two isolations from blood with the same anticoagulant were performed on blood from different donors (A or B). One quarter of the DNA obtained from 10 μl of blood is shown in the upper part of the figure, except for heparin, where half the DNA obtained from 5 μl is shown. 20 of the product from PCR reactions started with 10% of the isolated DNA is shown in the lower part of the figure, except for heparin, where 20% of the isolated DNA was used as starting material.

FIG. 8 shows the effect of sample storage conditions. Panel I shows Dynabeads DNA DIRECT isolations from EDTA blood that has been used fresh, refrigerated for 4 days, or frozen for 4 days. The two isolations from blood with the same storage conditions were performed on blood from different donors. Half of the DNA obtained from 10 µl of blood is shown in the upper part of the figure, 20% of the product from PCR reactions started with 10 µl of the isolated DNA is shown in the lower part of the figure. Panel II shows Dynabeads DNA DIRECT isolations from citrate blood that has been used fresh or air dried and rehydrated. The two isolations from blood with the same storage conditions were performed on blood from different donors. Half of the DNA obtained from 10-µl of blood is shown in the upper part of the figure, 20% of the product from PCR reactions started with 10% of the isolated DNA is shown in the lower part of the figure.

FIG. 9 shows Dynabeads DNA DIRECT from bone marrow and culture cells. Panel I shows Dynabeads DNA DIRECT isolations from 1, 2 and 5 µl of bone marrow from each of two donors. A or B above the lanes denote the identity of the donor. Half of the DNA obtained is shown in the upper part of the figure, 20% of the product from PCR reactions started with 10% of the isolated DNA is shown in the lower part of the figure. Panel II shows two Dynabeads DNA DIRECT isolations from $4 \times 10^5$ Daudi cells. One tenth of the DNA obtained is shown in the upper part of the figure, 20% of the product from PCR reactions started with 1 µl of a total of 120 µl isolated DNA is shown in the lower part of the figure. The molecular weight marker is λHindIII for the genomic DNA and 100 bp ladder for the PCR products.

Figure 10:
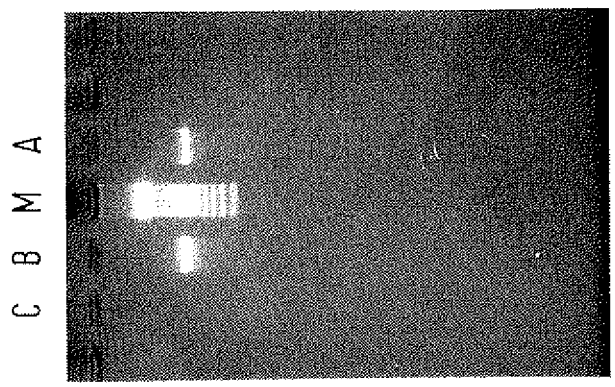

FIG. 10 shows Dynabeads DNA DIRECT from formalin fixed, paraffin embedded material. Lane A is 20% of the PCR product from a reaction started with DNA isolated by DNA DIRECT from a formalin fixed, paraffin embedded section of liver. Lane M is molecular weight marker (100 bp ladder), lane B is positive control (PCR from 20 ng human DNA), and lane C is negative control (PCR from water).

Figure 11:
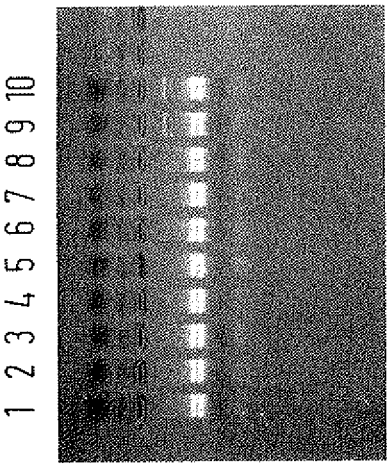

FIG. 11 shows Dynabeads DNA DIRECT for mRNA purification. mRNA was isolated from 1 million Daudi cells per sample with Dynabeads Oligo(dT)$_{25}$ after removal of DNA with Dynabeads DNA DIRECT. Increasing amounts of DNA DIRECT Dynabeads were used to remove genomic DNA; 1 mg in lane 1 and 2; 2 mg in lane 3 and 4; 5 mg in lane 5 and 6 and 10 mg in lane 7 and 8. Lane 9 and 10 are controls where no DNA was removed before direct mRNA purification. The extra bands on the top of the picture show contaminating genomic DNA in lane 9 and 10. The two strong bands in all lanes represent ribsomal RNA.

Figure 12:
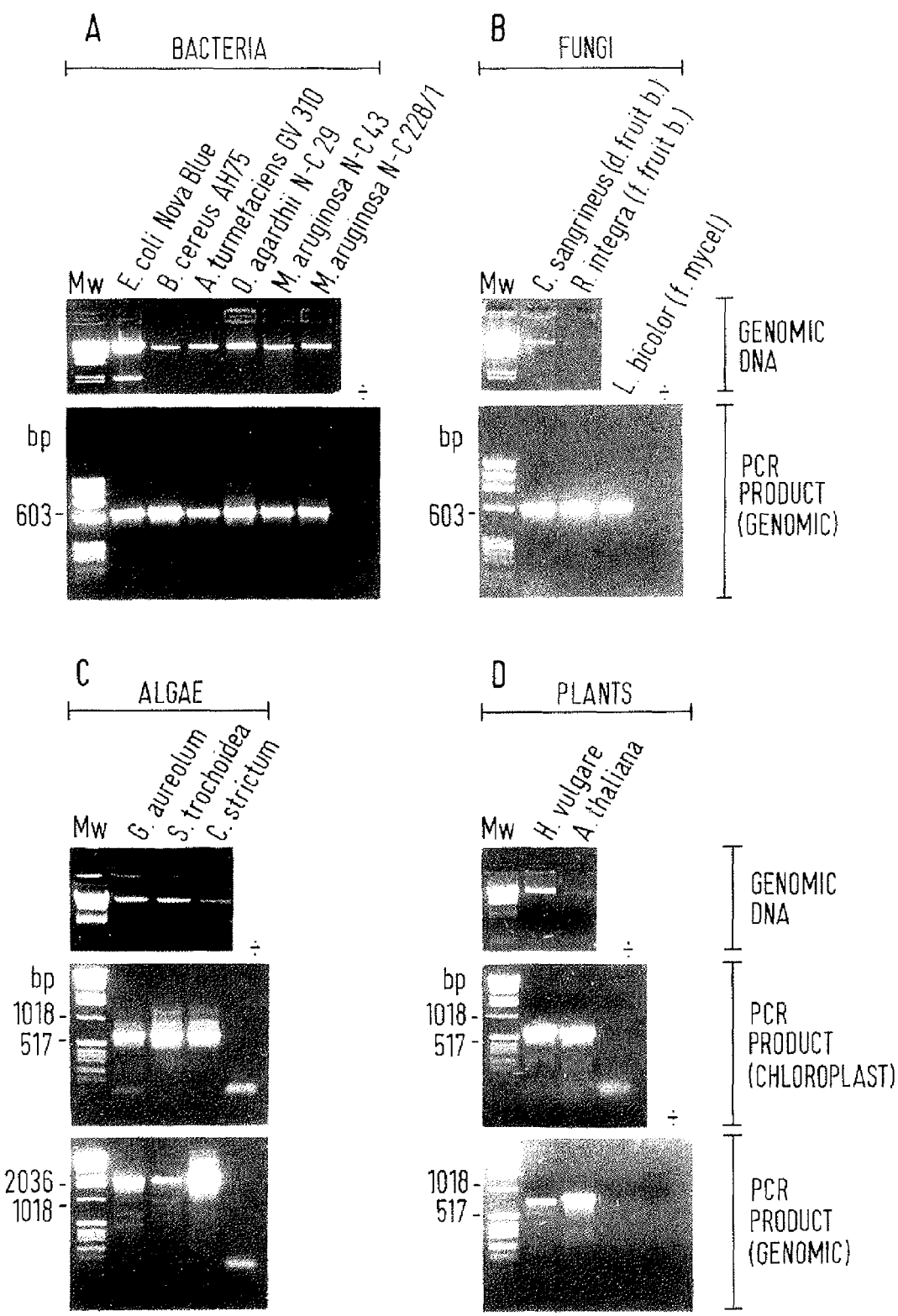

FIG. 12, shows the results of DNA isolation and PCR amplification from (A) bacteria, (B) fungi, (C) algae and (D) plants. For all samples, DNA was isolated with 200 µl DNA DIRECT (one sample test) and 20% of the isolated DNA and 10% of the PCR products were analysed by agarose electrophoresis. For bacteria, 2.5% of the isolated DNA was used per PCR reaction, for the other samples 5% was used. 16S rRNA regions were amplified from bacterial genomic DNA and from algae chloroplast DNA. From fungi- and algae genomic DNA, 18S rDNA were amplified. Amplification of the group I intron chloroplast trnL and parts of the genomic B15C gene are shown for plants. The negative controls are PCR on samples without DNA prepared in the same way as the other reactions.

EXAMPLE 1

Figure 2:
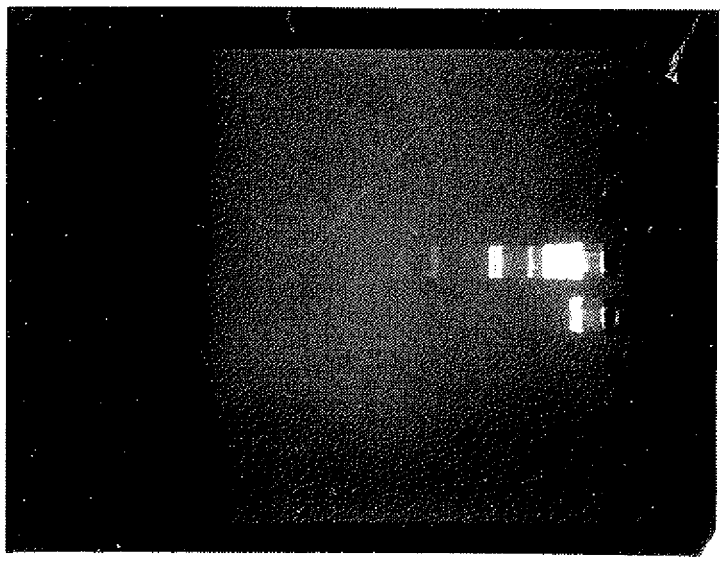
FIG. 2 shows gel electrophoresis of a sample of DNA isolated as described in Example 1 (lane 1: isolation; lane 2: λHind III (molecular weight marker))

DNA Isolation from Cell Culture $4 \times 10^6$ HL60 cells were washed twice in PBS and pelleted. The pellet was dissolved in 10 µl PBS, and 1 mg of Dynabeads® M-280* obtainable by autoclaving a suspension of Dynabeads® M-280 tosylactivated (available from DYNAL A/S, Oslo, Norway) in water) resuspended in 0.1 ml lysis buffer [5% SDS/10 mM TrisCl pH 8.0/1 mM EDTA] was added. This was followed immediately by the addition of 1 ml lysisbuffer, and the suspension was incubated for 5 minutes at room temperature, after which the Dynabeads®, with bound DNA was attracted to a magnet and the liquid phase removed. The solid phase was then washed twice with 1 ml washing buffer [50 mM NaCl/10 mM TrisCl pH 8.0/1 mM EDTA]. Finally, the beads, with bound DNA, were resuspended in 0.1 ml water, and incubated for 5 minutes at 65° C. The beads were attracted to a magnet, and the liquid phase withdrawn. The liquid phase was then analyzed for its DNA content. Results from an optical density scan (FIG. 1) are in accordance with pure DNA. The $OD_{260}/OD_{280}$ ratio is 1.72; pure DNA in water or TE has a ratio of 1.7-1.9. With pure DNA, the concentration can be determined from the $OD_{260}$ of the solution. A 50 µg/ml solution has $OD_{260}=1.0$. From the $OD_{260}$ measurement (Table 1) of 0.436 (0.1 ml total volume, 10 mm lightpath), the yield can be calculated to 2.18 µg DNA, 82% of the 2.67 µg that was the estimated DNA content of the starting material. Gel electrophoresis of a sample of the isolated DNA (FIG. 2) shows that most of it is in a high molecular weight form (>20 kb).

TABLE 1

PERKIN-ELMER LAMBDA BIO UV/VIS SPECTROMETER
APPLICATION NO. 3: RATIO 260/280 NM

| SAMPLE | CYCLE | WAVELENGTH AUTOZERO | DATA | UNIT |
|---|---|---|---|---|
| 004 | 15:50 | 260.0 nm | 0.436 | ABS |
|  | 15:56 | 280.0 nm | 0.253 | ABS |
|  |  | RATIO | 1.723 | RAT |

EXAMPLE 2

Isolation of DNA from Whole Blood and Enzymatic Application without Elution

5 µl whole blood (EDTA blood) was lysed in 50 µl 5% SDS and 50 µg Dynabeads® M-280* in 5 µl of PBS was added. The lysate was incubated for 1 minute at room temperature before 0.5 ml TrisCl pH 7.5 was added. The lysate was then incubated for 1 minute further at room temperature before the beads with bound DNA were attracted to a magnet and the liquid phase removed. The beads were then washed once with 0.5 ml 10 mM TrisCl pH 7.5, before the beads with bound DNA was resuspended in 40 µl TE (10 mM TrisCl pH 8.0/1 mM EDTA). 4 µl of the isolation was used in starting material for PCR (GAPDH PCR as described in Example 7). The PCR reaction gave large amounts of product, as visualised on agarose gel electrophoresis (FIG. 3). 10 µl of a 50 µl PCR reaction was loaded on the gel.

EXAMPLE 3

Example 1 was repeated using the following combination of lysisbuffers and washing buffers, and the following results were obtained:

| Lysis buffer | Washing buffer | Result |
|---|---|---|
| 2% SDS | 50 mM NaCl/1 × TE | +++ |
| 2% SDS/1 × TE | 50 mM NaCl/1 × TE | +++ |
| 2% SDS/1 × TE/10 mM NaCl | 50 mM NaCl/1 × TE | +++ |
| 5% SDS | 50 mM NaCl/1 × TE | +++ |

-continued

| Lysis buffer | Washing buffer | Result |
|---|---|---|
| 5% SDS/1 × TE | 50 mM NaCl/1 × TE | +++ |
| 5% SDS/1 × TE/10 mM NaCl | 50 mM NaCl/1 × TE | +++ |
| 1% LiDS/10 × TE/0.5M LiCl | 50 mM NaCl/1 × TE | +++ |
| 1% LiDS/10 × TE/0.5M LiCl | 150 mM LiCl/1 × TE | +++ |
| 5% LiDS | 150 mM LiCl/1 × TE | +++ |
| 5% SDS | 150 mM LiCl/1 × TE | +++ |
| 1% Sarcosyl | 150 mM LiCl/1 × TE | +++ |

(where +++ indicates very good DNA isolation)

1×TE is 10 mM TrisCl pH 8.0/1 mM EDTA, 10×TE is 100 mM TrisCl pH 8.0/10 mM EDTA

EXAMPLE 4

Following the procedure of Example 1, similar results may be achieved using Dynabeads® M-450 uncoated (Dynal A/S, Oslo, Norway)

EXAMPLE 5

Isolation of DNA from CD2 Positive Cells Obtained from Blood with Immunomagnetic Separation This experiment consisted of two identical isolations. 50 µl blood was mixed with 50 µl PBS [150 mM NaCl/10 mM NaH$_2$PO$_4$/Na$_2$HPO$_4$, pH 7.4] and 10 µl (4×10$^6$ beads) Dynabead® M-450 Pan-T (CD2) (available from Dynal AS, Oslo, Norway). The mixture was then incubated for 30 minutes at room temperature with gentle tilting and rotation. The cell/beads complex was attracted to a magnet and the fluid withdrawn. The cell/beads complex was then washed four times in 200 µl PBS, before 200 µg Dynabeads® M-280* (as above) and 200 µl lysisbuffer [100 mM Tris-HCl, pH 8.0/500 mM LiCl/10 mM EDTA, pH 8.01/1% LiDS] was added. The mixture was incubated for 5 minutes at room temperature, before the DNA/beads complex was attracted to a magnet, and the supernatant withdrawn. The DNA/beads complex was washed twice with 200 µl washing buffer [10 mM Tris-Hcl, pH 8.0/150 mM LiCl/1 mM EDTA, pH 8.0] and resuspended in 50 µl water. After 5 minutes at 65° C., the beads were attracted to a magnet and the supernatant transferred to a new tube. 5 µl of the supernatant was used as template for polymerase chain reaction (GAPDH PCR as described in Example 7), which gave large amounts of product, as visualised on agarose gel electrophoresis (FIG. 4).

EXAMPLE 6

Comparison of Yield and Integrity Between DNA Isolated by a Traditional Method and the Present Method Using a traditional method based on phenol extraction and ethanol precipitation, genomic DNA was isolated from 5 ml of EDTA anticoagulated blood. Four isolations from 10 µl of the same blood sample were performed using Dynabeads DNA DIRECT (kit, commercially available from Dynal AS, Oslo, Norway, containing beads equivalent to Dynabeads® M-280* as described in Example 1). The DNA from two of the isolations was eluted for 5 minutes at 65° C., while the DNA from the other two isolations was left in the presence of the Dynabeads. All the DNA from the four Dynabeads DNA DIRECT isolations was loaded onto an agarose gel, as was 0.2% of traditionally isolated DNA. The fraction of the traditionally isolated DNA loaded corresponds to the yield from 10 µl of blood (0.2% of 5 ml).

Traditional DNA isolation was performed according to the method of John and coworkers (John, S. W. M., G. Weitzner, R. Rosen and C. R. Scriver. 1991. A Rapid Procedure for Extracting Genomic DNA from Leukocytes. Nucl. Acid. Res. 19(2):408).

With Dynabeads DNA DIRECT, lysis of the blood was obtained by mixing 200 µl (one sample test) of Dynabeads DNA DIRECT with 10 µl of blood in a 1.5 ml microcentrifuge tube (200 µg uncoated Dynabeads in Lysis/binding buffer). Lysates were then left on the bench at room temperature for 5 minutes to allow adsorption of genomic DNA to the Dynabeads.

The DNA/Dynabeads complex was attracted to a magnet (Dynal's Magnetic Particle Collector E (MPC-E)), and the lysate was aspirated and discarded.

The complex was then washed twice in washing buffer (one of the kit components) by attracting it to a Dynal MPC and discarding the supernatant. Finally, the complex was resuspended in 10 µl of TE pH 8.0 (provided in the kit).

When elution was performed, it consisted of heating the suspension to 65° C. for five minutes and then attracting the beads to a magnet. The DNA-containing aqueous phase was then withdrawn and used for the experiments.

The DNA was visualised on ethidium bromide stained 1.5% agarose gels. Electrophoresis was performed in 1×TAE buffer, and the results were documented with a DS34 Polaroid camera and Polaroid 667 film.

The result of this experiment is shown in panel I of FIG. 5. The yield per µl blood is similar with the two methods (lane 1-4 vs lane 5-6), and very little DNA is lost during the elution step (lane 1-2 vs lane 3-4). The molecular weight of the DNA from both methods is more than 20 kb, as it runs slower than the 23.13 kb band of the λHindIII molecular weight marker.

DNA DIRECT was used to isolate DNA from ACD blood from two different donors, one male and one female. From each of the isolations, 10% was used as starting material for PCR amplification of an amplicon in the X-Y homologous amelogenin (AMXY) gene (Akane, A., K, Matsubara, H. Nakamura, S. Takahashi and K. Kimura. 1994. Purification of Highly Degraded DNA by Gel Filtration for PCR. BioTechniques 16 (2):235-238), as was 200 ng from each of two traditional DNA isolations.

DNA DIRECT and traditional DNA isolation was performed as described in the first part of this example.

All PCR reactions were performed in a 50 µl reaction volume, 10×PCR buffer (Perkin Elmer) was added to a final concentration of 1×, dNTPs (Pharmacia) were added to a final concentration of 0.2 mM, and 1 unit of amplitaq (Perkin Elmer) was used per reaction. 5 pmol each of primers AMXY-1F (5'-CTGATGGTTGGCCTCAAGCCT-GTG-3') and AMXY-4R (5'-TTCATTGTAAGAGCAAAGCAAACA-3') were added per reaction. PCR was performed on a Perkin Elmer GeneAmp PCR System 9600. PCR conditions for the AMXY amplicon were 4 min at 94° C., 38×[30 sec at 94° C., 30 sec at 55° C., 1 min at 72° C.], 10 min at 72° C.

10 µl of the 50 µl PCR reactions were visualised on ethidium bromide stained 1.5° agarose gels. Electrophoresis was performed in 1×TAE buffer, and the results were documented with a DS34 Polaroid camera and Polaroid 667 film.

The results of this experiment are shown in panel II of FIG. 5. The X-Y homologous amelogenin gene is known to be sensitive to DNA degradation (Akane et al 1994, supra). With increasing degradation, the 908 bp long X band gets progressively weaker as compared to the 719 bp long Y band. From panel II of FIG. 5 it is apparent that the relative strength of the X and Y bands is comparable for DNA isolated with Dynabeads DNA DIRECT and the traditional method, indicating that the degree of degradation is the same with the two methods. The PCR reactions from traditionally isolated DNA gives somewhat more product than does the reactions from DNA DIRECT isolated DNA. The reason for this is that ten times more template is used in the PCR reactions from traditionally isolated DNA than in the PCR reactions from DNA DIRECT isolated DNA.

Lysis/binding buffer: 0.5 M LiCl
   1% LiDS
   0.1 M TrisCl pH 7.5
   10 mM EDTA
   5 mM dithiothreitol (DTT)
Washing buffer: 0.15 M LiCl
   10 mM Tris-HCl pH 8.0
   1 mM EDTA

EXAMPLE 7

Five Independent DNA Isolations from Blood Samples from Each of Two Donors

For this experiment, we used Dynabeads DNA DIRECT kit, which is commercially available from Dynal AS, Oslo, Norway. Buffer compositions are as described in example 6.

Five DNA isolations were performed from each of two citrate treated blood samples of relatively low white blood cell counts (sample A: $3.6 \times 10^6$ cells/ml, sample B: $2.6 \times 10^6$ cells/ma).

Lysis of the blood was obtained by mixing 200 µl (one sample test) of Dynabeads DNA DIRECT with blood in a 1.5 ml microcentrifuge tube. Lysates were then left on the bench at room temperature for 5 minutes to allow adsorption of genomic DNA to the Dynabeads.

The DNA/Dynabeads complex was attracted to a magnet (Dynal's Magnetic Particle Collector E (MPC-E)), and the lysate was aspirated and discarded.

The complex was then washed twice in washing buffer (one of the kit components) by attracting it to a Dynal MPC and discarding the supernatant. Finally, the complex was resuspended in 40 µl of TE pH 8.0 (provided in the kit). This resuspension was used for PCR and gel electrophoresis without any elution.

From each isolation, 10% was used as starting material for PCR amplification of an amplicon in the glyceraldehyde phosphate dehydrogenase (GAPDH) gene. All PCR reactions were performed in a 50 µl reaction volume, 10×PCR buffer (Perkin Elmer) was added to a final concentration of 1×, dNTPs (Pharmacia) were added to a final concentration of 0.2 mM, and 1 unit of amplitaq (Perkin Elmer) was used per reaction. 5 pmol each of primers GAPDH-Forward (5'-ACAGTCCATGCCATCACTGCC-3') and GAPDH-Reverse (5'-GCCTGCTTCACCACCTTCTTG-3') were added per reaction. PCR was performed on a Perkin Elmer GeneAmp PCR System 9600. PCR conditions for the GAPDH amplicon were 4 min at 94° C., 34×[30 sec at 94° C., 30 sec at 61° C., 1 min at 72° C.], 10 min at 72° C.

Both genomic DNA and PCR products were visualised on ethidium bromide stained 1.5% agarose gels. 10 µl of the 50 µl reaction was loaded on to an agarose gel, as was 50% of the isolated genomic DNA. Electrophoresis was performed in 1×TAE buffer, and the results were documented with a DS34 Polaroid camera and Polaroid 667 film.

The results of this experiment are shown in FIG. 6. No significant variation between the different isolations can be observed. Similar results were obtained with other coagulants as well as from donors with higher white blood cell counts.

EXAMPLE 8

DNA Isolation from Blood with Different Anticoagulants

Dynabeads DNA DIRECT (kit, commercially available from Dynal AS, Oslo, Norway) was used to isolate DNA from untreated whole blood as well as blood anticoagulated with EDTA, Citrate or Heparin. From each type of starting material, two separate isolations were performed, with blood from different donors. The buffer components in the kit are as described in example 6.

Lysis of the DNA containing cells from blood was obtained by mixing 200 µl (one sample test) of Dynabeads DNA DIRECT with 5 µl Heparin blood or 10 µl of other blood samples in a 1.5 ml microcentrifuge tube. Lysates were then left on the bench at room temperature for 5 minutes to allow adsorption of genomic DNA to the Dynabeads.

The DNA/Dynabeads complex was attracted to a magnet (Dynal's Magnetic Particle Collector E (MPC-E)), and the lysate was aspirated and discarded.

The complex was then washed twice in washing buffer (one of the kit components) by attracting it to a Dynal MPC and discarding the supernatant. Finally, the complex was resuspended in 20-40 µl of TE pH 8.0 (provided in the kit). We used 40 µl as the standard volume, but 20 µl if the starting material was Heparin blood.

From each isolation, 10% (20% from the Heparin samples) was used as starting material for PCR amplification of an amplicon in the glyceraldehyde phosphate dehydrogenase (GAPDH) gene. PCR was performed directly on the suspension in TE, with the Dynabeads present. All PCR reactions were performed in a 50 µl reaction volume, 10×PCR buffer (Perkin Elmer) was added to a final concentration of 1×, dNTPs (Pharmacia) were added to a final concentration of 0.2 mM, and 1 unit of amplitaq (Perkin Elmer) was used per reaction. 5 pmol each of primers GAPDH-Forward (5'-ACAGTCCATGCCATCACTGCC-3') and GAPDH-Reverse (5'-GCCTGCTTCACCACCTTCTTG-3') were added per reaction. PCR was performed on a Perkin Elmer GeneAmp PCR System 9600. PCR conditions for the GAPDH amplicon were 4 min at 94° C., 34×[30 sec at 94° C., 30 sec at 61° C., 1 min at 72° C.], 10 min at 72° C.

10 µl of the 50 µl reaction was loaded on to an agarose gel, as was 25% (50% from the Heparin samples) of the isolated genomic DNA. Both genomic DNA and PCR products were visualised on ethidium bromide stained 1.5% agarose gels. Electrophoresis was performed in 1×TAE buffer, and the results were documented with a DS34 Polaroid camera and Polaroid 667 film.

The results of this experiment are shown in FIG. 7. As the isolations from Heparinized samples were from only 5 µl of blood, using 20% of the DNA from these isolations as starting material for PCR is comparable to using 10% from the other isolations, that are all from 10 µl blood. When this is taken into consideration, it is apparent that the type of anticoagulant used does not significantly affect the result.

In the experiment just described, Lithium Heparin was used. In this system, similar results are obtained with Lithium and Sodium Heparin, even though Lithium Heparin has been shown to have inhibitory effects in other systems (Panaccio, M., M. Georgesz and A. M. Lew. 1993. FoLT PCR: A Simple PCR Protocol for Amplifying DNA Directly from Whole Blood. BioTechniques 14(3): 238-243). DNA DIRECT also performs well on blood anticoagulated with ACD (panel II of FIG. 5) or CPD (data not shown).

EXAMPLE 9

Isolation of DNA from Blood Samples Stored Under Different Conditions

Dynabeads DNA DIRECT (kit, commercially available from Dynal AS, Oslo, Norway) was used to isolate DNA from EDTA blood from two different donors: What was remaining of the blood samples were then divided into two, one part that was stored at +4° C. and one that was stored at −20° C. After 4 days, the frozen samples were thawed, and DNA was isolated from both the frozen samples and the samples that had been kept at +4° C. The buffer components of the kit are as described in example 6.

Lysis of the blood was obtained by mixing 200 μl (one sample test) of Dynabeads DNA DIRECT with blood in a 1.5 ml microcentrifuge tube. Lysates were then left on the bench at room temperature for 5 minutes to allow adsorption of genomic DNA to the Dynabeads.

The DNA/Dynabeads complex was attracted to a magnet (Dynal's Magnetic Particle Collector E (MPC-E)), and the lysate was aspirated and discarded.

The complex was then washed twice in washing buffer (one of the kit components) by attracting it to a Dynal MPC and discarding the supernatant. Finally, the complex was resuspended in 40 μl of TE pH 8.0 (provided in the kit). Both PCR and agarose gel electrophoresis was performed directly on the suspension in TE, with the Dynabeads present.

From each of the 6 isolations (fresh, refrigerated, and frozen), 10% was used as starting material for PCR amplification of the GAPDH amplicon as described in example 8. Both genomic DNA and PCR products were visualised on ethidium bromide stained 1.5% agarose gels. 10 μl of the 50 μl reaction was loaded on the gel, as was 50% of the isolated genomic DNA. Electrophoresis was performed in 1×TAE buffer, and the results were documented with a DS34 Polaroid camera and Polaroid 667 film. The results of this experiment are shown in panel I of FIG. 8. No adverse effect of 4 days storage at +4 or −20° C. was observed in this system. Using Dynabeads DNA DIRECT as described earlier in this example, DNA was isolated from two citrate treated blood samples, and from the same two samples 10 μl was spotted on a plastic surface and allowed to air dry at room temperature. The dried blood spots were transferred to 1.5 ml tubes, 40 μl PBS was added, and the tubes were left at room temperature with gentle agitation for 90 min, before DNA was isolated with Dynabeads DNA DIRECT. From each of the 4 isolations (fresh and dried), 10% was used as starting material for PCR amplification of the GAPDH amplicon as described in example 8. Both genomic DNA and PCR products were visualised on ethidium bromide stained 1.5% agarose gels. 10 μl of the 50 μl reaction was loaded on the gel, as was 50% of the isolated genomic DNA. Electrophoresis was performed in 1×TAE buffer, and the results were documented with a DS34 Polaroid camera and Polaroid 667 film. The results of this experiment are shown in panel II of FIG. 8. The yield from dried blood is good and the isolated DNA is suitable for PCR.

EXAMPLE 10

DNA Isolation from Bone Marrow and Culture Cells

DNA Isolations from Bone Marrow 1, 2, and 5 μl of heparinized bone marrow from each of two healthy donors were used as starting material for DNA isolation with DNA DIRECT. The buffer components are as described in example 6. Lysis of the bone marrow was obtained by mixing 200 μl (one sample test) of Dynabeads DNA DIRECT with 1-5 μl of heparinized bone marrow in a 1.5 ml microcentrifuge tube. Lysates were then left on the bench at room temperature for 5 minutes to allow adsorption of genomic DNA to the Dynabeads.

The DNA/Dynabeads complex was attracted to a magnet (Dynal's Magnetic Particle Collector E(MPC-E)), and the lysate was aspirated and discarded.

The complex was then washed twice in washing buffer (one of the kit components) by attracting it to a Dynal MPC and discarding the supernatant. Finally, the complex was resuspended in 40 μl of TE pH 8.0 (provided in the kit). Both PCR and agarose gel electrophoresis was performed directly on the suspension in TE, with the Dynabeads present.

From each of the 6 isolations, 10% was used as starting material for PCR amplification of the GAPDH amplicon as described in example 8.

Both genomic DNA and PCR products were visualised on ethidium bromide stained 1.5% agarose gels. 10 μl of the 50 μl reaction was loaded on to an agarose gel, as was 50% of the isolated genomic DNA. Electrophoresis was performed in 1×TAE buffer, and the results were documented with a DS34 Polaroid camera and Polaroid 667 film.

The results of this experiment are shown in panel I of FIG. 9. It is apparent from panel I of FIG. 9 that the yield per volume starting material is higher from bone marrow than from blood (FIGS. 5-8). This is to be expected, since the concentration of DNA containing cells is much higher in bone marrow than in blood. 5 μl of bone marrow is close to the upper limit of what can be handled by 1 sample test of DNA DIRECT. A good correlation between sample size and DNA yield is observed in the 1 to 5 μl sample size interval, but even the yield from 1 μl is sufficient for at least 10 PCR reactions.

DNA Isolation from Cultured Cells

Two samples of $4 \times 10^5$ Daudi cells were used as starting material for DNA isolation with DNA DIRECT. DNA isolation from $4 \times 10^5$ cultured cells (cell line Daudi) was performed as described above, except that 1 ml (five sample tests) of Dynabeads DNA DIRECT was used. Accordingly, the washing steps were performed in 1 ml washing buffer. The DNA/Dynabeads complex was resuspended in 120 μl TE, and as for bone marrow, no elution step was performed after the resuspension.

From each of the isolations, 1 μl of a total of 120 μl was used as starting material for PCR amplification of the GAPDH amplicon, as described in Example 8.

Both genomic DNA and PCR products were visualised on ethidium bromide stained 1.5% agarose gels. 10 μl of the 50 μl reaction was loaded on to an agarose gel, as was 10% of the isolated genomic DNA. Electrophoresis was performed in 1×TAE buffer, and the results were documented with a DS34 Polaroid camera and Polaroid 667 film.

The results of this experiment are shown in panel II of FIG. 9, demonstrating that at least 120 PCR reactions may be run from an isolation of this scale.

EXAMPLE 11

Isolation of DNA from a Formalin Fixed, Paraffin Embedded Section of Liver

Dynabeads DNA DIRECT (kit, commercially available from Dynal AS, Oslo, Norway) was used to isolate DNA from a formalin fixed, paraffin embedded section of liver. The buffer components of the kit and the bead concentration are as described in example 6.

Excess paraffin was removed from the edges of the sample with a scalpel blade. Lysis of the sample was obtained by adding 200 µl (one sample test) of Dynabeads DNA DIRECT to the sample in a 1.5 ml microcentrifuge tube. Lysates were then left on the bench at room temperature for 5 minutes to allow adsorption of genomic DNA to the Dynabeads. The lysate, containing DNA and Dynabeads was transferred to a fresh tube, leaving cell debris and paraffin behind.

The DNA/Dynabeads complex was attracted to a magnet (Dynal's Magnetic Particle Collector E (MPC-E)), and the lysate was aspirated and discarded.

The complex was then washed twice in washing buffer (one of the kit components) by attracting it to a Dynal MPC and discarding the supernatant. Finally, the complex was resuspended in 10 µl of sterile water. This suspension, with the Dynabeads present, was used as starting material for PCR amplification of the GAPDH amplicon as described in example 8. The PCR product was visualised on an ethidium bromide stained 1.5% agarose gel. 10 µl of the 50 µl reaction was loaded on the gel. Electrophoresis was performed in 1×TAE buffer, and the results were documented with a DS34 Polaroid camera and Polaroid 667 film. The result of this experiment is shown in FIG. 10. PCR amplifiable material has clearly been obtained from the formalin fixed, paraffin embedded section of liver.

EXAMPLE 12

Removal of Genomic DNA with DNA Direct Prior to mRNA Isolation mRNA was isolated from 1 million Daudi cells per sample. The cells were lysed in 0.75 ml Lysis/binding buffer with DNA DIRECT Dynabeads present in the buffer. The samples were incubated for 5 minutes and the DNA-Dynabead complexes were collected by applying a Dynal MPC-E magnet for 2 minutes. Different amounts of DNA DIRECT beads were used to remove genomic DNA; 1, 2, 5 and 10 mg per sample (FIG. 11).

The lysate from each sample was transferred to new tubes with 1 mg Dynabeads Oligo(dT)$_{25}$ according to standard procedure (Dynals mRNA DIRECT kit protocol). The Dynabeads were mixed with the lysate to capture the polyadenylated mRNA by hybridisation for 5 minutes at room temperature. The mRNA-Dynabead complexes were collected with the MPC-E magnet by placing the tubes in the magnetic stand for 2 minutes. The solution was removed and discarded. Washing solution with LiDS (0.75 ml) was added and the beads were washed thoroughly by pipetting up and down. The mRNA-Dynabead complexes were collected with the magnet, and the washing procedure was repeated once with washing buffer with LiDS and twice with washing buffer without detergent. Finally, the purified mRNA was eluted from the Dynabeads in 20 µl 5 mM Tris-HCl pH 7.5 buffer, by incubation at 65° C. for 2 minutes. The eluates were analysed by non-denaturing gel electrophoresis in a 1.0% agarose gel with ethidium bromide. FIG. 11 shows the results from this experiment.

The EtBr-staining reveals both double-stranded DNA and rRNA due to secondary structure. The two ribosomal RNA bands are clearly visible in all lanes. In Lane 9-10 in FIG. 11, some genomic DNA is present as contamination after the mRNA purification procedure. In the recommended mRNA procedure from DYNAL, a DNA-shearing step is introduced after cell lysis, to reduce the possibility of DNA contamination. By using DNA removal with DNA DIRECT beads this shearing step is not necessary.

Lysis/binding buffer: 0.5 M LiCl
    1% LiDS
    0.1 M TrisCl pH 7.5
    10 mM EDTA
    5 mM dithiothreitol (DTT)
Washing buffer with LiDS: 0.15 M LiCl
    0.1% LiDS
    10 mM Tris-HCl pH 8.0
    1 mM EDTA
Washing buffer: 0.15 M LiCl
    10 mM Tris-HCl pH 8.0
    1 mM EDTA

EXAMPLE 13

Universal Method for DNA Isolation

PCR-Ready DNA from Bacteria, Fungi, Algae, Plants and Vertebrates

*E. coli* and *Baceillus cereus* were grown overnight at 37° C. in LB medium, *Agrobacterium tumefaciens* was grown overnight in YEB medium for about 40 hours at 28° C. (Sambrook, J. et al., 1989, Molecular Cloning: A Laboratory Manual, 2nd ed., Cold Spring Harbour Laboratory, NY.). Cyanobacteria and Prochlorthrix were grown in NIVA medium for 14 days at 18° C. using an illumination of 20 micro Einstein (Norwegian Institute of Water Research, 1991, Culture collection of algae). 20-200 million bacteria or 450,000 cyanobacteria were used per DNA isolation.

Agar plates containing 2% malt extract was used for mycelia growth and incubated for 14 days at room temperature. Mycelia was isolated by scraping the surface of the agar plates with a spatula. Fungi fruitbodies were obtained from natural populations. In the range of 1-3 mg air dried and 3-20 mg fresh fungi fruitbodies were used per DNA isolation.

Bakers yeast *Saccharomyces cerevisiae* was obtained from a commercial supplier. Algae were cultured under illumination in IMR-medium for 7 days (Eppley, R et al., 1967, Exp. Mar. Biol. Ecol. 1, 191-208). Fresh leaves from *Arabidopsis thaliana* and barley (*Hordeum vulgare*) were picked from young plants (3 weeks old). Epithelia were obtained from perch (*Perca fluvatilis*) fins. About 1 mg wet weight yeast, 30-100 mg young plant leaves and 100-400 mg perch were used per DNA isolation.

Multicellular tissues with rigid cell walls were mechanically broken to increase DNA yield. Fungi fruitbodies were ground with forceps for about 2 minutes. Plant leaves were homogenised for 2 minutes in liquid nitrogen with a pestle (Kontes Scientific Instruments, Vineland, N.J., USA). For all other samples no mechanical work was required for cell breakage.

DNA Isolation

DNA isolations were performed using Dynabeads DNA DIRECT (kit, commercially available from Dynal AS, Oslo, Norway). Lysis of the cells and organisms were obtained by mixing 200 µl of Dynabeads DNA DIRECT (200 µg uncoated Dynabeads in Lysis/binding buffer) with the sample in a 1.5 ml microcentrifuge tube. Lysates were then left on the bench at room temperature for 5 to 15 minutes to allow adsorption of genomic DNA to the Dynabeads. For some bacteria and for plants, incubation at 65° C. for 15 minutes was used to improve lysis before the adsorption step.

The DNA/Dynabeads complex was attracted to a magnet (Dynal's Magnetic Particle Collector E (MPC-E)), and the lysate was aspirated and discarded.

The complex was then washed twice in washing buffer (one of the kit components) by attracting it to a Dynal MPC and discarding the supernatant. Finally, the complex was resuspended in 40 µl of TE pH 8.0 (provided in the kit) by vigorous pipetting. Elution was performed by heating the suspension to 65° C. for five minutes and then attracting the beads to a magnet. The DNA-containing aqueous phase was then withdrawn and used for the experiments.

The DNA was visualised on ethidium bromide stained 1.5% agarose gels. Electrophoresis was performed in 1×TAE buffer, and the results were documented with a DS34 Polaroid camera and Polaroid 667 film.

Lysis/binding buffer: 0.5 M LiCl
  1% LiDS
  0.1 M TrisCl pH 7.5
  10 mM EDTA
  5 mM dithiothreitol (DTT)
Washing buffer: 0.15 M LiCl
  10 mM Tris-HCl pH 8.0
  1 mm EDTA For an evaluation of the yield from the DNA DIRECT isolation protocol, standard phenol/chloroform based methods were used. Algae, vertebrate and bacterial DNA were isolated with the protocol described by Sambrook, J. et al., 1989, supra. Cyanobacteria were homogenized with alumina type A-5 (Sigma Chemicals Co., St. Louis, USA) before isolation to ensure complete lysis. Plant and fungi DNA were isolated with the protocol described by Scot, O. R. and Bendich, A. J., 1994, in "Plant Molecular Biology Manual", page D1: 1-8, Kluwer Academic Publisher, Belgium.

PCR Amplifications

For each sample type the reproducibility was tested by using separate DNA isolations, serial DNA dilutions and multiple PCR assays. DNA isolation reagents and PCR reagents were controlled for absence of contamination in each separate experiment. All PCR reactions were performed in a 50 µl reaction volume containing; 15 pmoles primers, 200 µM dNTP, 10 mM Tris-HCl pH 8.8, 1.5 mM MgCl$_2$, 50 mM KCl, 0.1% Triton X-100, 1 Unit DynaZyme thermostable polymerase (Finnzymes Oy, Finland) and 0.1-5 µl of isolated DNA. PCR was performed on a Perkin Elmer GeneAmp PCR System 9600.

Amplicons and Oligonucleotide Primers

All PCR reactions were started with a DNA denaturation step at 94-97° C. for 3 to 5 minutes and ended with an extension step at 72° C. for 5 minutes.

Bacteria and Algae:

The amplicon was a 16S rRNA region corresponding to *E. coli* base 334 to 939 according to IUD numbering from bacteria and algae chloroplasts (Brosius, J., et al., 1978, Proc. Natl. Acad. Sci., USA, 57, 4801-4805).
Primers: CC 5'-TGTAAAACGACGGCCAGTCCAGACTC-CTACGGGAGGCAGC-3'
  CD 5'-CTTGTGCGGGCCCCCGTCAATTC-3'

Primer CC has a 5' end complementary to −21 M13 universal primer, making it suitable for direct DNA sequencing. Amplification: 30 cycles of 96° C. for 15 seconds and 70° C. for 2 minutes.

Algae: An 18S rRNA region was amplified with the primers A and B described by Medlin et al., 1990, Gene, 71, 491-499.

Amplification: 35 cycles of 94° C. for 30 seconds, 50° C. for 1 minute and 72° C. for 1 minute.

Fungi: A 18S rRNA region (ca. 600 bp.) was amplified with the primers NS3 and NS4 as described by White et al., 1990. In "PCR Products, a Guide to Methods and Applications" by Innis, M. A. et al., page 315-322, Academic Press, New York.

Amplification: 5 cycles of 94° C. for 30 seconds, 53° C. for 30 seconds and 72° C. for 1 minute; followed by 25 cycles of 94° C. for 30 seconds, 50° C. for 30 seconds increasing with 15 seconds for each cycle, and 72° C. for 1 minute.

Plants: The tRNL group I intron in chloroplasts were amplified with the primers C and D described by Fangan et al., 1994, BioTechniques 16, 484-494.

Amplification: 30 cycles of 94° C. for 30 seconds, 55° C. for 30 seconds and 72° C. for 1 minute.

A part of the *Arabidopsis thaliana* gene BI5C (800 bp) was amplified with the primers 5'-CGGGATCCCTAGGAGA-CACGGTGCCG-3' and 5'-GGAATTCGATCGGCGGTCT-TGAAAC-3'

Amplification: 35 cycles of 94° C. for 30 seconds, 59° C. for 30 seconds and 72° for 1 minute.

A part of the Barley gene B15C (800 bp) was amplified with the primers 5'-CGGATCCCGTCATCCTCTTCTCG-CACCCC-3' and 5'-GGAATTCCCTTCTTGGAGGGCAG-GTCGGCG-3'.

Amplification: 35 cycles of 94° C. for 30 seconds, 60° C. for 30 seconds and 72° C. for 1 minute.

Perch: Mitochondrial D-loop fragment (800-900 bp) was amplified with the primers HV2 described by Hoelzel et al., 1991, Mol. Biol. Evol., 8, 475-493, and the primer 5'-GGT-GACTTGCATGTGTAAGTTCA-3'.

Amplification: 30 cycles of 96° C. for 1 minute, 52° C. for 2 minutes and 72° C. for 2 minutes.

The amplified fragments were visualised on ethidium bromide stained 1.5% agarose gels. Electrophoresis was performed in 1×TAE buffer, and the results were documented with a DS34 Polaroid camera and Polaroid 667 film.

The results of the experiments are shown in FIG. 12 and Table 2.

Bacteria: The standard protocol gave DNA yields in the range of 100-1000 ng for the bacteria tested (FIG. 12A). For some Cyanobacteria there was a substantial increase in DNA yield (from 500 ng to more than 1 mg) by improving the lysis with an extra initial incubation step at 65° C. for 15 minutes. In all cases, good amplifications were obtained by using 0.25% of the isolated DNA.

Fungi: The highest DNA yield was obtained from dried fruit-bodies (300-500 ng) compared with fresh fruit bodies (100-200 ng) (FIG. 12B). Mycelia gave low DNA recovery probably due to low number of cells per sample. However, in most cases 5% of the isolated DNA was enough to give nice PCR products (Table 2, FIG. 12B). For fruit bodies, 0.5-5% of DNA was used for each PCR.

Algae: All algae tested gave DNA yield in the range of 200-400 ng using the standard protocol and 1 DNA DIRECT sample test (Table 2, FIG. 12C). Nice PCR results were obtained both for amplification of genomic DNA and chloroplast DNA by using 5% of the isolated DNA per PCR reaction.

Plants: To obtain good DNA yield from plant leaves homogenization in liquid nitrogen was necessary. An extra initial incubation step at 65° C. for 15 minutes also improved the results (FIG. 12D). Nice PCR results were obtained both for amplification of genomic DNA and chloroplast DNA, when 5% of the isolated DNA was used per PCR reaction.

Fish: DNA yield of 300-500 ng was routinely obtained from fish epithelia, using the standard protocol and one sample test (Table 2). Mitochondrial DNA was nicely amplified using 5% of the isolated DNA.

PCR products from all species tested could easily be directly sequenced by solid-phase sequencing (Hultman et al., 1989, Nucleic Acids Res., 17, 4937-4946).

TABLE 2

DNA isolation and PCR amplification from different organisms

| Species[a] | | Sample[b] | DNA yield[c] | Amplicon[d] Gen. Org. | PCR product[e] |
|---|---|---|---|---|---|
| Bacteria | | | | | |
| *Bacillus sereus* AH 75[a] | gram pos. | fresh | +++ | 16S | +++ |
| *E. coli* NovaBlue[1] | | fresh | +++ | 16S | +++ |
| *A. tumefaciens* GV 310[8] | | fresh | +++ | 16S | +++ |
| *Planktothrix agardhii* N-C 29 | | fresh | +++ | 16S | +++ |
| *P. prolifica* N-C320 | gram neg. | fresh | +++ | 16S | +++ |
| *Microsystis aruginosa* N-C 43 | | fresh | +++ | 16S | +++ |
| *M. aruginosa* N-C 228/1 | Cyanobacteria | fresh | +++ | 16S | +++ |
| *Anabaena bory* N-C 246 | | frozen | +++ | 16S | ++ |
| *Phormidium sp* N-C 177 | | frozen | +++ | 16S | ++ |
| *Aphanizomenon sp* N-C 103 | | frozen | +++ | 16S | +++ |
| *P. hollandica* N 5/89 | prochlorthrix | frozen | ++ | 16S | +++ |
| Fungi | | | | | |
| *Cortinarius sanguineus* | | d.fruitb. | +++ | 18S | +++ |
| *Cortinarius gentilis* | basidiomycetes | d.fruitb. | nt | 18S | +++ |
| *Russula integra* | | f.fruitb. | ++ | 18S | +++ |
| *Laccaria bicolor* | | f.mycel | + | 18S | +++ |
| *Triharia ochroleuca* | | f.mycel | nt | 18S | +++ |
| *Verjahinia cabhae* | ascomycetes | f.mycel | nt | 18S | +++ |
| *Peziza vesiculosa* | | f.mycel | nt | 18S | +++ |
| *Saccharomyces cevisiae* | yeast | fresh | + | 18S | +++ |
| Algae | | | | | |
| *Gyrodinum aureolum* | | fresh | +++ | 18S/16S | +++/+++ |
| *Hetrocapsa triguerta* | | fresh | +++ | 18S/16S | +++/+++ |
| *Scripsiella trochidea* | dinoflagellates | fresh | +++ | 18S/16S | +++/+++ |
| *Ceramium strictum* | | fresh | +++ | 18S | +++ |
| *Chlorella vulgaris* | | fresh | +++ | 18S | +++ |
| *Clamydomonas reinardii* | chlorophyta | fresh | +++ | 18S | +++ |
| *Caulacantus ustulata* | phacophceae | fresh | +++ | 18S | +++ |
| *Chrysochromulina polylepis* | crysophyceae | fresh | +++ | 18S | +++ |
| Plants | | | | | |
| *Hordeum vulgare* (barly) | monocot | leaf | +++ | B15C/trnL | +++/+++ |
| *Arabidopsis thaliana* | dicot | leaf | +++ | B15C/trnL | +++/+++ |
| Vertebrates | | | | | |
| *Perca fluvatilis* (perch) fish | | ep. | +++ | D-loop | +++ |

[a]*A. tumerfaciens* = *Aghrobacterium tumefaciens*,

*P. hollandica* = *Prochlorothrix hollandica*.

[b]d.fruitb = dried fruitbodies, f.mycelia = fresh mycelia, ep. = epithelium.

[c]Approximate DNA yields relative to standard phenol/chloroform isolations;

+++: >80%,

++: >10%,

+: >1%, nt. = not tested.

[d]Gen. = genomic DNA,

Org. organelle DNA from chloroplasts (algae and plants) and mitochondria (fish).

[e]Amplicons as described in example 13.

The invention claimed is:

1. A method of using a particulate solid support for isolating nucleic acid from a sample comprising:
contacting said sample with a detergent and the particulate solid support in the absence of a chaotropic agent,
allowing soluble nucleic acid in said sample to bind directly to the solid support thereby forming a particulate solid support with bound nucleic acid, wherein the binding of the soluble nucleic acid to the solid support is independent of nucleic acid sequence and the binding is non-covalent; and
separating said particulate solid support with bound nucleic acid from the sample, wherein the particulate solid support is not linked to an antibody and wherein the particulate support is not a filter.

2. The method of claim 1, wherein the nucleic acid is DNA.

3. The method of claim 2, wherein the nucleic acid is genomic DNA.

4. The method of claim 1, wherein the nucleic acid is RNA.

5. The method of claim 1, wherein the detergent is anionic.

6. The method of claim 5, wherein the detergent is sodium dodecyl sulphate, or another alkali metal alkylsulphate salt, or sarkosyl.

7. The method of claim 1, wherein the concentration of detergent is 0.2 to 30% (w/v).

8. The method of claim 1, wherein the detergent is contained in a composition additionally comprising one or more monovalent cations, chelating agents or reducing agents.

9. The method of claim 1, wherein the detergent is used in alkaline solution.

10. The method of claim 1, wherein the particulate solid support comprises beads.

11. The method of claim 10, wherein the particulate solid support comprises non-magnetic polymer beads.

12. The method of claim 10, wherein the particulate solid support comprises magnetic beads.

13. The method of claim 1, wherein the solid support has a hydrophobic surface.

14. The method of claim 1, further comprising one or more additional steps to disrupt structural components in the sample or to achieve lysis of cells in the sample.

15. The method of claim 1, wherein the nucleic acid is eluted from the support, following separation from the sample.

16. The method of claim 7, wherein the nucleic acid is eluted by heating.

17. The method of claim 1, wherein the particulate solid support comprises glass or silica.

* * * * *

SEQUENCE LISTING

<160> NUMBER OF SEQ ID NOS: 13

<210> SEQ ID NO 1
<211> LENGTH: 24
<212> TYPE: DNA
<213> ORGANISM: Artificial
<220> FEATURE:
<223> OTHER INFORMATION: Primer

<400> SEQUENCE: 1
ctgatggttg gcctcaagcc tgtg                                              24

<210> SEQ ID NO 2
<211> LENGTH: 24
<212> TYPE: DNA
<213> ORGANISM: Artificial
<220> FEATURE:
<223> OTHER INFORMATION: Primer

<400> SEQUENCE: 2
ttcattgtaa gagcaaagca aaca                                              24

<210> SEQ ID NO 3
<211> LENGTH: 21
<212> TYPE: DNA
<213> ORGANISM: Artificial
<220> FEATURE:
<223> OTHER INFORMATION: Primer

<400> SEQUENCE: 3
acagtccatg ccatcactgc c                                                 21

<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4
gcctgcttca ccaccttctt g                                                 21

<210> SEQ ID NO 5
<211> LENGTH: 21
<212> TYPE: DNA
<213> ORGANISM: Artificial
<220> FEATURE:
<223> OTHER INFORMATION: Primer

<400> SEQUENCE: 5
acagtccatg ccatcactgc c                                                 21

<210> SEQ ID NO 6
<211> LENGTH: 21
<212> TYPE: DNA
<213> ORGANISM: Artificial
<220> FEATURE:
<223> OTHER INFORMATION: Primer

<400> SEQUENCE: 6
gcctgcttca ccaccttctt g                                                 21

<210> SEQ ID NO 7
<211> LENGTH: 40
<212> TYPE: DNA

```
<213> ORGANISM: Artificial
<220> FEATURE:
<223> OTHER INFORMATION: Primer

<400> SEQUENCE: 7
tgtaaaacga cggccagtcc agactcctac gggaggcagc                            40

<210> SEQ ID NO 8
<211> LENGTH: 23
<212> TYPE: DNA
<213> ORGANISM: Artificial
<220> FEATURE:
<223> OTHER INFORMATION: Primer

<400> SEQUENCE: 8
cttgtgcggg cccccgtcaa ttc                                              23

<210> SEQ ID NO 9
<211> LENGTH: 26
<212> TYPE: DNA
<213> ORGANISM: Artificial
<220> FEATURE:
<223> OTHER INFORMATION: Primer

<400> SEQUENCE: 9
cgggatccct aggagacacg gtgccg                                           26

<210> SEQ ID NO 10
<211> LENGTH: 25
<212> TYPE: DNA
<213> ORGANISM: Artificial
<220> FEATURE:
<223> OTHER INFORMATION: Primer

<400> SEQUENCE: 10
ggaattcgat cggcggtctt gaaac                                            25

<210> SEQ ID NO 11
<211> LENGTH: 29
<212> TYPE: DNA
<213> ORGANISM: Artificial
<220> FEATURE:
<223> OTHER INFORMATION: Primer

<400> SEQUENCE: 11
cggatcccgt catcctcttc tcgcacccc                                        29

<210> SEQ ID NO 12
<211> LENGTH: 30
<212> TYPE: DNA
<213> ORGANISM: Artificial
<220> FEATURE:
<223> OTHER INFORMATION: Primer

<400> SEQUENCE: 12
ggaattccct tcttggaggg caggtcggcg                                       30

<210> SEQ ID NO 13
<211> LENGTH: 23
<212> TYPE: DNA
<213> ORGANISM: Artificial
<220> FEATURE:
<223> OTHER INFORMATION: Primer

<400> SEQUENCE: 13
ggtgacttgc atgtgtaagt tca                                              23
```